US009427544B2

(12) United States Patent
Frater et al.

(10) Patent No.: US 9,427,544 B2
(45) Date of Patent: Aug. 30, 2016

(54) PATIENT INTERFACE

(71) Applicant: ResMed Limited, Bella Vista, New South Wales (AU)

(72) Inventors: Robert Henry Frater, Sydney (AU); Quangang Yang, Sydney (AU); Paul Anthony Green, Sydney (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 14/389,689

(22) PCT Filed: Mar. 28, 2013

(86) PCT No.: PCT/AU2013/000324

§ 371 (c)(1),
(2) Date: Sep. 30, 2014

(87) PCT Pub. No.: WO2013/142909

PCT Pub. Date: Oct. 3, 2013

(65) Prior Publication Data

US 2015/0059759 A1 Mar. 5, 2015

Related U.S. Application Data

(60) Provisional application No. 61/617,908, filed on Mar. 30, 2012.

(30) Foreign Application Priority Data

Jan. 25, 2013 (NZ) ........................................ 606253

(51) Int. Cl.
*A61M 16/06* (2006.01)
*A61M 16/04* (2006.01)
(Continued)

(52) U.S. Cl.
CPC ..... *A61M 16/0666* (2013.01); *A61M 16/0003* (2014.02); *A61M 16/0488* (2013.01);
(Continued)

(58) Field of Classification Search
CPC .................... A61M 16/0666; A61M 16/0488; A61M 16/06; A61M 16/0638; A61M 16/0003; A61M 16/0622; A61M 16/20; A61M 16/0694; A61M 16/0875; A61M 16/0069; A61M 16/0493
See application file for complete search history.

(56) References Cited

U.S. PATENT DOCUMENTS

| | | | |
|---|---|---|---|
| 5,560,354 | A | 10/1996 | Berthon-Jones et al. |
| 6,123,071 | A | 9/2000 | Berthon-Jones et al. |

(Continued)

FOREIGN PATENT DOCUMENTS

| | | |
|---|---|---|
| DE | 37 19 009 | 12/1988 |
| EP | 0 264 772 | 4/1988 |

(Continued)

OTHER PUBLICATIONS

"Effect of Nasal or Oral Breathing Route on Upper Airway Resistance During Sleep", Fitzpatrick et al. Eur Respir J 2003; 22: 827-832.

(Continued)

*Primary Examiner* — Justine Yu
*Assistant Examiner* — Timothy Stanis
(74) *Attorney, Agent, or Firm* — Nixon & Vanderhye P.C.

(57) ABSTRACT

A patient interface for treatment of a user having a respiratory disorder includes a nasal portion having at least one nasal portion aperture adapted to be in communication with a supply of pressurized gas for delivery to at least one nasal opening of the user, and a mouth portion having at least one mouth portion aperture also adapted to be in communication with the supply of pressurized gas to deliver the pressurized gas to an oral cavity of the user's mouth. The at least one mouth portion aperture is separate from the at least one nasal portion aperture, and the patient interface is adapted to limit a flow of the pressurized gas out of the at least one aperture of the mouth portion to be no greater than a flow of the pressurized gas out of the at least one nasal portion aperture.

34 Claims, 37 Drawing Sheets

(51) Int. Cl.

| | |
|---|---|
| ***A61M 16/20*** | (2006.01) |
| ***A61M 16/00*** | (2006.01) |
| ***A61M 16/08*** | (2006.01) |

(52) U.S. Cl.

CPC ......... *A61M16/06* (2013.01); *A61M 16/0622* (2014.02); *A61M 16/0638* (2014.02); *A61M 16/0694* (2014.02); *A61M 16/0875* (2013.01); *A61M 16/20* (2013.01); *A61M 16/0069* (2014.02); *A61M 16/0493* (2014.02); *A61M 2016/003* (2013.01); *A61M 2016/0027* (2013.01); *A61M 2205/3334* (2013.01); *A61M 2209/06* (2013.01); *A61M 2210/0625* (2013.01)

(56) References Cited

U.S. PATENT DOCUMENTS

| | | | | |
|---|---|---|---|---|
| 7,318,439 | B2 | 1/2008 | Raje et al. | |
| 7,448,386 | B2 | 11/2008 | Ho et al. | |
| 7,669,599 | B2 | 3/2010 | Gunaratnam et al. | |
| 7,958,893 | B2 | 6/2011 | Lithgow et al. | |
| 8,028,699 | B2 | 10/2011 | Ho et al. | |
| 8,136,525 | B2 | 3/2012 | Lubke et al. | |
| 8,347,886 | B2 | 1/2013 | Ho et al. | |
| 2003/0024530 | A1 | 2/2003 | Sniadach | |
| 2004/0226563 | A1* | 11/2004 | Xu et al. | 128/206.21 |
| 2006/0054168 | A1* | 3/2006 | Yu | 128/206.29 |
| 2006/0237017 | A1* | 10/2006 | Davidson et al. | 128/205.25 |
| 2006/0283461 | A1* | 12/2006 | Lubke et al. | 128/207.11 |
| 2007/0006879 | A1* | 1/2007 | Thornton | 128/203.29 |
| 2007/0044804 | A1* | 3/2007 | Matula et al. | 128/206.21 |
| 2009/0114229 | A1 | 5/2009 | Frater et al. | |
| 2009/0133696 | A1* | 5/2009 | Remmers et al. | 128/204.26 |
| 2009/0159084 | A1* | 6/2009 | Sher | A61M 16/06 128/205.24 |
| 2009/0277452 | A1 | 11/2009 | Lubke et al. | |
| 2010/0307502 | A1 | 12/2010 | Rummery et al. | |
| 2011/0315143 | A1 | 12/2011 | Frater | |
| 2012/0145158 | A1 | 6/2012 | Lubke et al. | |
| 2013/0199537 | A1 | 8/2013 | Formica et al. | |

FOREIGN PATENT DOCUMENTS

| | | |
|---|---|---|
| EP | 0 634 186 | 1/1995 |
| EP | 0 634 186 B1 | 8/2000 |
| EP | 2 020 978 | 2/2009 |
| GB | 2 385 533 | 8/2003 |
| WO | WO 03/090827 | 11/2003 |
| WO | WO 2005/063328 | 7/2005 |
| WO | PCT/AU2006/001246 | 8/2006 |
| WO | WO 2006/130903 | 12/2006 |
| WO | WO 2007/008725 | 1/2007 |
| WO | PCT/AU2010/000381 | 4/2010 |
| WO | WO 2011/022751 | 3/2011 |
| WO | WO 2012/040791 | 4/2012 |
| WO | WO 2012/040792 | 4/2012 |

OTHER PUBLICATIONS

International Search Report issued in PCT Appln. No. PCT/AU2013/000324 mailed May 31, 2013.

First Examination Report issued in corresponding New Zealand Appln. No. 606253 dated Jan. 31, 2013.

First Examination Report issued in corresponding New Zealand Appln. No. 627433 dated Jul. 29, 2014.

Supplementary Partial European Search Report issued in corresponding European Application No. 13 76 9660.5 dated Oct. 13, 2015.

Extended European Search Report issued in corresponding European Application No. EP 13 76 9660.5 dated Feb. 1, 2016 including the Supplementary European Search Report and the European Search Opinion (11 pages).

Further Examination Report issued in corresponding New Zealand Application No. 627433 dated Nov. 24, 2015.

* cited by examiner 58
55
54
56
52
60
80
92
94
80.1
86
78
64
87
67
88
69
74
68

PATIENT INTERFACE

1. CROSS-REFERENCE TO RELATED APPLICATIONS

This application is the U.S. national phase of International Application No. PCT/AU2013/000324 filed 28 Mar. 2013, which designated the U.S. and claims priority to U.S. Provisional Application No. 61/617,908, filed Mar. 30, 2012, and also claims the benefit of New Zealand patent application 606253 filed 25 Jan. 2013, the entire contents of each of which are incorporated herein by reference in their entirety.

2. BACKGROUND OF TECHNOLOGY

2.1 Field of Technology

The present technology relates to a patient interface used for Non-invasive Positive Pressure Ventilation (NPPV) and for continuous positive airway pressure (CPAP) therapy of sleep disordered breathing (SDB) conditions such as obstructive sleep apnea (OSA).

2.2 Description of Related Art

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Pressurized air is delivered to the mask by a conduit connected to the CPAP device and the mask.

Upper airway resistance during sleep and the propensity to obstructive sleep apnoea are said to be significantly lower while breathing nasally rather than orally. See Fitzpatrick et al. *Eur Respir J* 2003; 22: 827-832.

While healthy subjects with normal nasal resistance are said to breathe almost exclusively through the nose during sleep, some patients nevertheless experience mouth breathing or occasional mouth leaks if they wear nasal-only masks, and such mouth breathing or mouth leak can be uncomfortable and/or reduce the effectiveness of treatment.

To address this, patients may use chin straps or tape to block the mouth. Other patients may use a nose and mouth, or full-face mask and receive pressurized air flows to the airways via the nose and mouth.

U.S. Pat. Nos. 5,560,354 and 6,123,071 (both to Berthon-Jones, and assigned to ResMed Limited) disclose a combination mouth and nasal mask for assisted respiration of CPAP.

EP Patent 2020978 (Respcare) is said to disclose a hybrid ventilation mask with a nasal interface and method for configuring such a mask.

International Patent Application No. PCT/AU2006/001246 published as WO 2007/025329 (to Frater et al., and assigned to ResMed Limited) discloses a mouth seal assembly for a nasal mask system to prevent mouth breathing.

International Patent Application No. PCT/AU2010/000381 published as WO 2010/111749 (to Frater, and assigned to ResMed Limited) discloses a nasal mask system including an interface adapted to form an air interface with a patient's nose, and a mouth seal adapted to form a seal with the patient's mouth to reduce or eliminate mouth breathing.

3. BRIEF SUMMARY OF TECHNOLOGY

One aspect of one form of the present technology relates to a patient interface to limit mouth breathing for use in delivery of respiratory gases to the airways of the user.

Another aspect of the present technology relates to a patient interface that provides respiratory therapy via pressurized gas to both the nasal and oral (mouth) passages of a patient, but limits the flowrate of the pressurized gas to the patient's mouth to control mouth breathing.

In one form of the present technology, a supply of pressurised gas is provided to the nasal and oral passages of a patient, the flowrate of pressurised gas into the patient's mouth is permitted, but controlled to be an amount that is about the same as the flow rate of gas to the patient's nasal passages.

In one form of the present technology, a supply of pressurised gas is provided to the nasal and oral passages of a patient, but the flowrate of pressurised gas into the patient's mouth is controlled to be an amount that is less than the flow rate of gas to the patient's nasal passages.

In one form of the present technology, about half of the flow of pressurised gas received by the patient goes in through the oral passage, and about half of the flow of pressurised gas goes through the nasal passages.

In one form of the present technology, about 49% of the flow of pressurised gas received by the patient goes through the oral passage, and about 51% of the flow of pressurised gas goes through the nasal passages. In an alternative form, of the present technology an amount that is less than about half of the flow of pressurised gas that is received by the patient goes via the oral passage, while an amount that is more than about half of the flow of pressurised gas goes via the nasal passages. In another form of the present technology, about an amount that is in a range of about one third to less than about one half goes via the oral passage, while the remainder of the gas that is received by the patient is received via the nasal passages.

In one form of the present technology, between 5% and 49% of the flow of pressurised gas received by the patient goes through the oral passage, with the remaining flow going through the nasal passages.

In one form of the present technology, the flow of air to the mouth is in a range of about 10% to about 50% of the total flow of air to the patient.

In one form of the present technology, a seal apparatus is provided to surround the mouth of a patient and to form a seal therewith, but permitting a flow of air to the oral passage.

Another aspect of the present technology is a patient interface that provides little or no force in an anterior to posterior direction on a patient's mandible.

Another aspect of one form of the present technology is a patient interface for delivery of a supply of air at positive pressure from a source of pressurised breathable air, said patient interface allows a first flow rate of air to the nasal cavity from a first chamber via a first orifice, and a second flow rate of air to the oral cavity from a second chamber via a second orifice, wherein the patient interface allows a flow of air to the second chamber at a rate that exceeds a rate required for pressure equalisation between the first and second chambers and further wherein the patient interface restricts the flow rate of air to the patient via the second orifice to an amount that is less than the flow rate of air to the patient via the first orifice.

Another aspect of the present technology relates to a patient interface that provides respiratory therapy via pressurized gas to the nasal passages and mouth of a patient, and provides a plurality of patient selectable flow levels for the pressurized gas directed to the patient's mouth.

Another aspect of the present technology relates to a patient interface that provides respiratory therapy via pressurized gas to the nasal passages and mouth of a patient, and provides a plurality of patient selectable and/or removably replaceable mouth cushions each of which provides a different sized mouth portion aperture(s) to limit the flow of the pressurized gas to the patient's mouth.

Another aspect of the present technology relates to a retrofit kit for converting a nasal only patient interface that provides respiratory therapy via pressurized gas to a nasal and mouth patient interface.

Another aspect of the present technology relates to a patient interface including a nasal portion and a mouth portion. The nasal portion has at least one nasal portion aperture adapted to be in communication with a supply of pressurized gas for delivery to at least one nasal opening of the user, and in one form a pair of nasal portion apertures. The mouth portion has at least one mouth portion aperture also adapted to be in communication with the supply of pressurized gas to deliver the pressurized gas to an oral cavity of the user's mouth. The at least one mouth portion aperture is separate from the at least one nasal portion aperture, and the patient interface is adapted to limit a flow of the pressurized gas out of the at least one aperture of the mouth portion to be no greater than a flow of the pressurized gas out of the at least one nasal portion aperture.

Another aspect of the present technology relates to a patient interface for treatment of a user having a respiratory disorder, the patient interface including a nasal portion, a mouth portion and an adaptor. The nasal portion is adapted to be in communication with a supply of pressurized gas for delivery to at least one of the nasal openings of the user. The mouth portion is also adapted to be in communication with the source of pressurized gas, and the mouth portion has at least one aperture to deliver the pressurized gas to the oral cavity of the user's mouth. The adaptor couples the mouth portion to the nasal portion, the adaptor including a first conduit portion to convey the pressurized gas to an interior of the nasal portion, and a second conduit portion depending from the first conduit portion and adapted to convey pressurized gas to an interior of the mouth portion, wherein the adaptor includes structure adapted to limit a flow of the pressurized gas out of the at least one aperture of the mouth portion to be no greater than a flow of the pressurized gas to the nasal portion.

Another aspect of the present technology relates to a retrofit kit for converting a nasal-only mask for treatment of a user having a respiratory disorder to a mouth and nasal mask, the nasal only mask having a nasal portion adapted to provide a flow of pressurized gas to nares of the user and having an aperture (e.g., front, side) adapted to receive an elbow. The retrofit kit includes a mouth portion including a mouth chamber, an adaptor including a first conduit having a first end to connect with the aperture of the nasal portion, the first conduit having a second end adapted to receive the elbow, the adaptor having a second conduit extending from the first conduit and in pressure communication with the first conduit and the chamber of the mouth portion, and structure adapted to limit a flow of the pressurized gas out of the mouth portion to be no more than the flow of the pressurized gas provided out of the nasal portion to the nares of the user Another aspect of the present technology relates to a retrofit kit for converting a nasal-only mask for treatment of a user having a respiratory disorder to a mouth and nasal mask, the nasal only mask having a nasal portion with a nasal chamber adapted to provide a flow of pressurized gas to nares of the user, and having an aperture adapted to receive an elbow. The retrofit kit includes a mouth portion, structure adapted to connect the nasal portion to the mouth portion, an air delivery tube to connect the chamber of the nasal portion to the mouth portion, and flow limitation structure adapted to limit a flow of the pressurized gas out of the mouth portion to be no more than the flow of the pressurized gas provided out of the nasal portion to the nares of the user.

It should be appreciated that the above defined feature of limiting the flow of the pressurized gas passing through the mouth portion can be extended into introducing a mouth seal that completely closes the mouth portion in order to prevent any mouth breathing. Alternatively, the mouth flow restriction can be completely lifted to allow free mouth breathing when necessary, such as in the case of a patient having a blocked nose.

Other aspects, features, and advantages of the present technology will become apparent from the following detailed description when taken in conjunction with the accompanying drawings, which are a part of this disclosure and which illustrate, by way of example, principles of this technology.

4. BRIEF DESCRIPTION OF THE DRAWINGS

The accompanying drawings facilitate an understanding of the various examples of this technology. In such drawings:

4.1 Treatment Systems

FIG. 1*a* shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000. A bed partner 1100 is also shown. The PAP device 4000, humidifier 5000 and air circuit 4170 may be connected to a patient interface 3000 in accordance with the present technology.

4.2 Therapy 4.2.1 Respiratory System

FIG. 2*a* shows an overview of a human respiratory system including the nasal and oral cavities, the larynx, vocal folds, oesophagus, trachea, bronchus, lung, alveolar sacs, heart and diaphragm.

FIG. 2*b* shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.2.2 Facial Anatomy

FIG. 2*c* is a front view of a face with several features of surface anatomy identified including the lip superior, upper vermillion, lower vermillion, lip inferior, mouth width, endocanthion, a nasal ala, nasolabial sulcus and cheilion.

FIG. 2*d* is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

FIG. 2*e* is a further side view of a head. The approximate locations of the Frankfort horizontal and nasolabial angle are indicated.

FIG. 2*f* shows a base view of a nose.

FIG. 2*g* shows a side view of the superficial features of a nose.

FIG. 2*h* shows subcutaneal structures of the nose, including lateral cartilage, septum cartilage, greater alar cartilage, lesser alar cartilage and fibrofatty tissue.

FIG. 2*i* shows a medial dissection of a nose, approximately several millimeters from a sagittal plane, amongst other things showing the septum cartilage and medial crus of greater alar cartilage.

FIG. 2*j* shows a front view of the bones of a skull including the frontal, temporal, nasal and zygomatic bones. Nasal concha are indicated, as are the maxilla, mandible and mental protuberance.

FIG. 2*k* shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2*l* shows an anterolateral view of a nose.

4.3 Patient Interface

FIG. 3-2 depicts a front view of the patient interface of FIG. 3-1.

FIG. 3-3 depicts a rear view of the patient interface of FIG. 3-1.

FIG. 3-4 depicts a bottom view of the patient interface of FIG. 3-1.

FIG. 3-5 depicts a side view of the patient interface of FIG. 3-1.

FIG. 3-6 depicts a cross-sectional view of the patient interface of FIG. 3-1.

FIG. 3-7 depicts a view of a mouth portion of a patient interface according to an example of the present technology.

FIG. 3-8 depicts a view of the mouth portion of FIG. 3-7.

FIG. 3-9 depicts a top view of the mouth portion of FIG. 3-7.

FIG. 3-10 depicts a side view of the mouth portion of FIG. 3-7.

FIG. 3-11 depicts an exploded perspective view of the patient interface of FIG. 3-1.

FIG. 3-12 depicts a perspective view of a patient interface according to an example of the present technology.

FIG. 3-13 depicts a front view of a portion of the patient interface of FIG. 3-12.

FIG. 3-14 depicts a rear view of the patient interface of FIG. 3-12.

FIG. 3-15 depicts a top view of the patient interface of FIG. 3-12.

FIG. 3-16 depicts a bottom view of the patient interface of FIG. 3-12.

FIG. 3-17 depicts a side view of the patient interface of FIG. 3-12.

FIG. 3-18 depicts a cross-sectional view of the patient interface of FIG. 3-12.

FIG. 3-19 depicts an exploded perspective view of the patient interface of FIG. 3-12.

FIG. 3-20 depicts a perspective view of an adaptor according to an example of the present technology.

FIG. 3-21 depicts a front view of the adaptor of FIG. 3-20.

FIG. 3-22 depicts a cross-sectional view of the adaptor of FIG. 3-20.

FIG. 3-23 depicts a perspective view of a restrictor for use with the patient interface of FIG. 3-12.

FIG. 3-24 depicts a front view of the restrictor of FIG. 3-23.

FIG. 3-25 depicts a rear view of the restrictor of FIG. 3-23.

FIG. 3-26 depicts a side view of the restrictor of FIG. 3-23.

FIG. 3-27 depicts another side view of the restrictor of FIG. 3-23 with the aperture in a more closed position compared to the restrictor of FIG. 3-26.

FIG. 3-28 depicts a perspective view of a mask system according to an example of the present technology.

FIG. 3-29 depicts a rear view of a portion of the patient interface of FIG. 3-28.

FIG. 3-30 depicts a rear view of the patient interface of FIG. 3-28.

FIG. 3-31 depicts a top view of the patient interface of FIG. 3-28.

FIG. 3-32 depicts a bottom view of the patient interface of FIG. 3-28.

FIG. 3-33 depicts a side view of the patient interface of FIG. 3-28.

FIG. 3-34 depicts a cross-sectional view of the patient interface of FIG. 3-28.

FIG. 3-35 depicts an exploded side view of the patient interface of FIG. 3-28.

FIG. 3-36 depicts a perspective view of the adaptor of the patient interface of FIG. 3-28.

FIG. 3-37 depicts a rear view of the adaptor of FIG. 3-36.

FIG. 3-38 depicts a cross-sectional view of the adaptor of FIG. 3-36.

FIG. 3-39 depicts a perspective view of a restrictor according to an example of the present technology.

FIG. 3-40 depicts a front view of the restrictor of FIG. 3-39.

FIG. 3-41 depicts a top view of the restrictor of FIG. 3-39.

FIG. 3-42 depicts a perspective view of a mouth portion cushion having no mouth portion aperture according to an example of the present technology.

FIG. 3-43 depicts a perspective view of a mouth portion cushion having a single mouth portion aperture according to an example of the present technology.

FIG. 3-44 depicts a perspective view of a mouth portion cushion having two mouth portion apertures according to an example of the present technology.

FIG. 3-45 depicts a perspective view of a mouth portion cushion having four mouth portion apertures according to an example of the present technology.

FIGS. 3-46 and 3-47 depict various parameters relevant to the sealing operation of an example of the described patient interface.

4.4 PAP Device

Figure 4A:
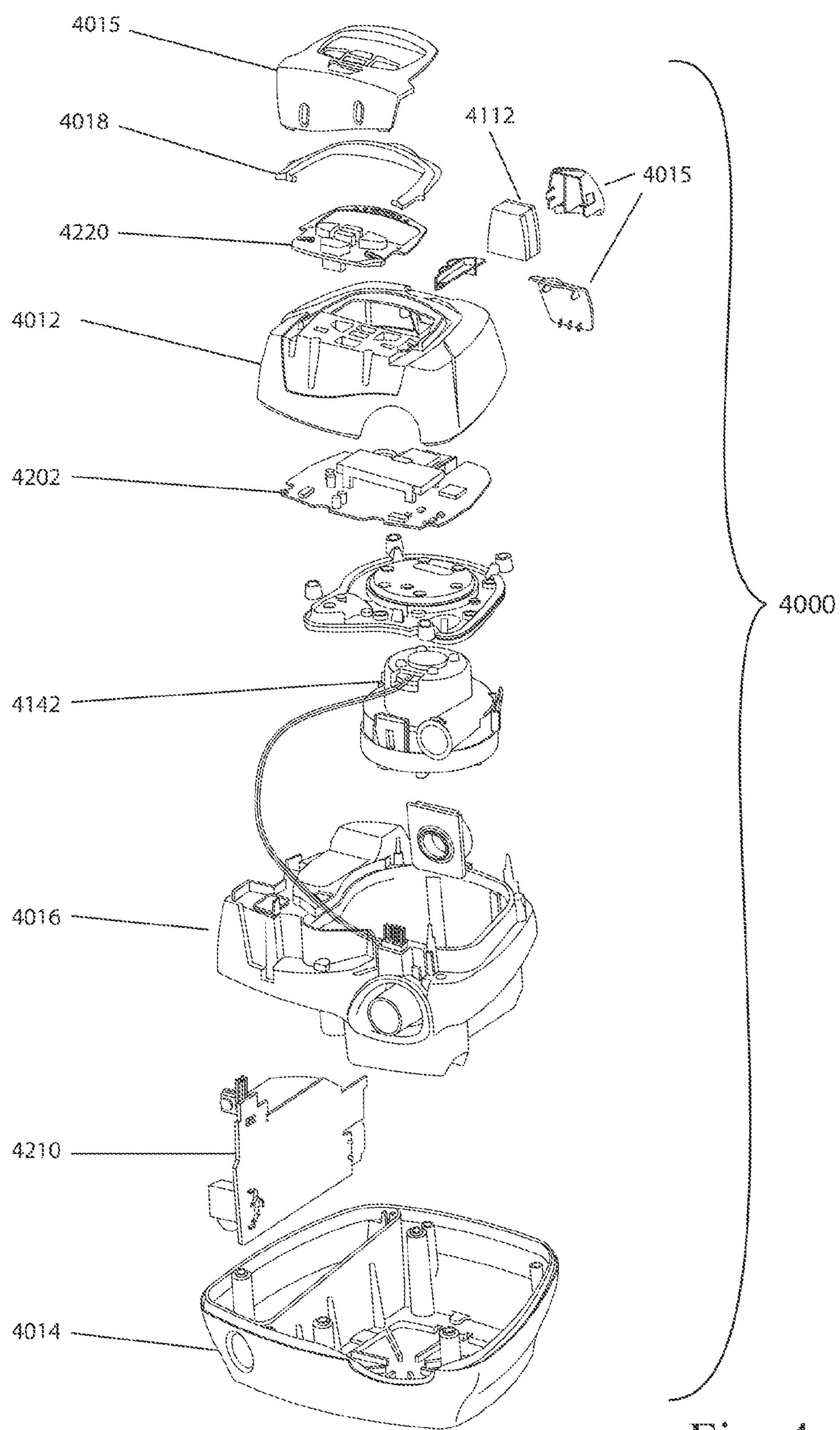

FIG. 4*a* shows a PAP device in accordance with one form of the present technology.

5. DETAILED DESCRIPTION OF ILLUSTRATED EXAMPLES

The following description is provided in relation to several examples which may share one or more common characteristics and features. It is to be understood that one or more features of any one example may be combinable with one or more features of the other examples. In addition, any single feature or combination of features in any of the examples may constitute additional subject matter Applicant(s) may independently pursue.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is acknowledged that the CPAP flow generator systems or blowers described herein may be designed to pump fluids other than air.

In this specification, a "nasal only" mask will be taken to mean a form of patient interface that delivers a supply of air or breathable gas to a patient to one or both of the nares of a patient, without also delivering a supply of air to the airways of the patient via the mouth.

5.1 Treatment Systems

In one form, the present technology comprises apparatus for ameliorating or treating a respiratory disorder. In an example, the apparatus comprises a flow generator or blower for supplying pressurised respiratory gas, such as air, to the patient 1000 via an air delivery tube leading to a patient interface 3000 (e.g., see FIG. 1*a*). In one form, the apparatus is a CPAP system, in other forms the apparatus is a ventilator.

5.2 Therapy

Figure 1A:
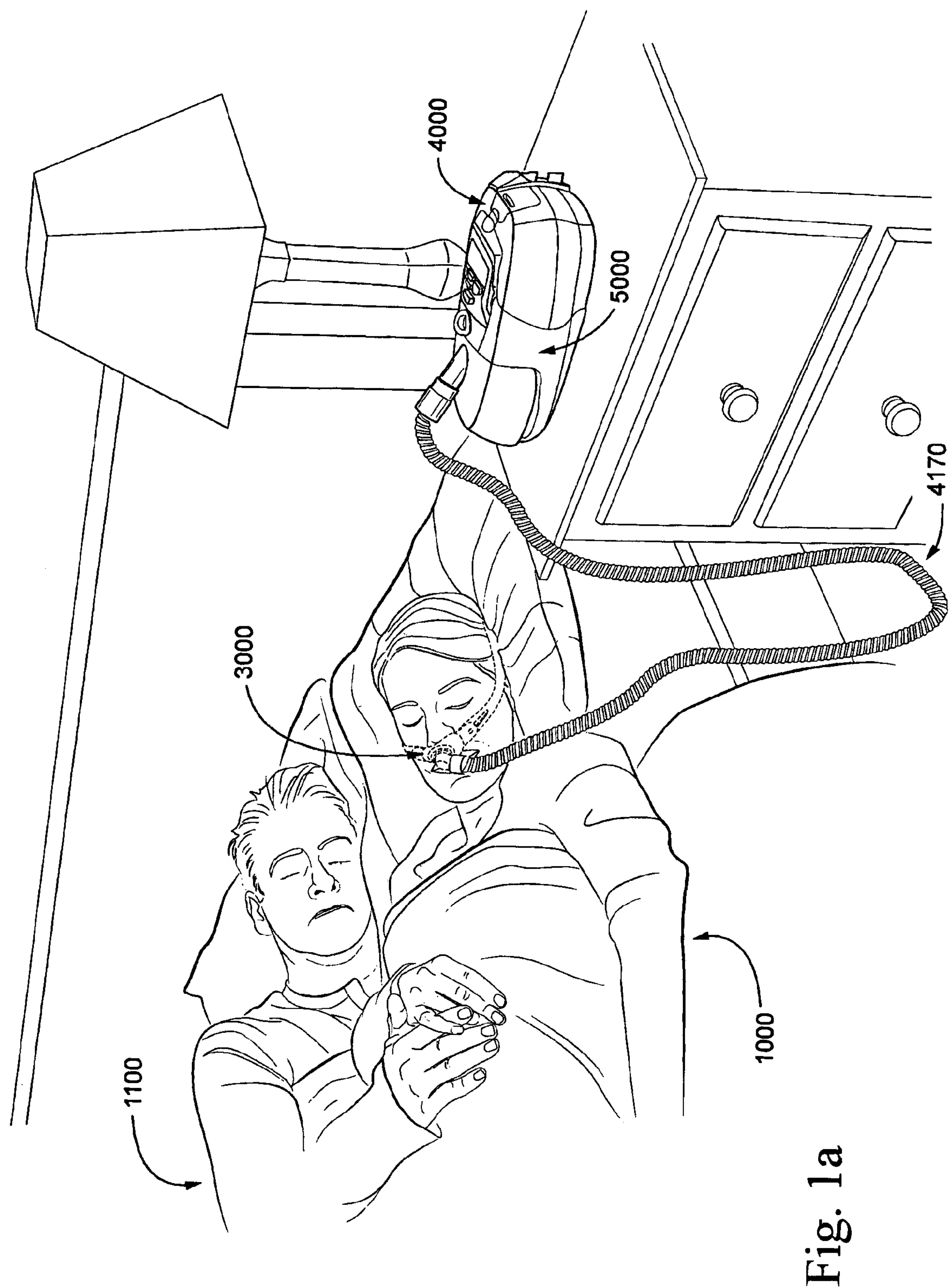
FIG. 3-1 depicts a perspective view of a patient interface according to an example of the present technology.
Figure 2A:
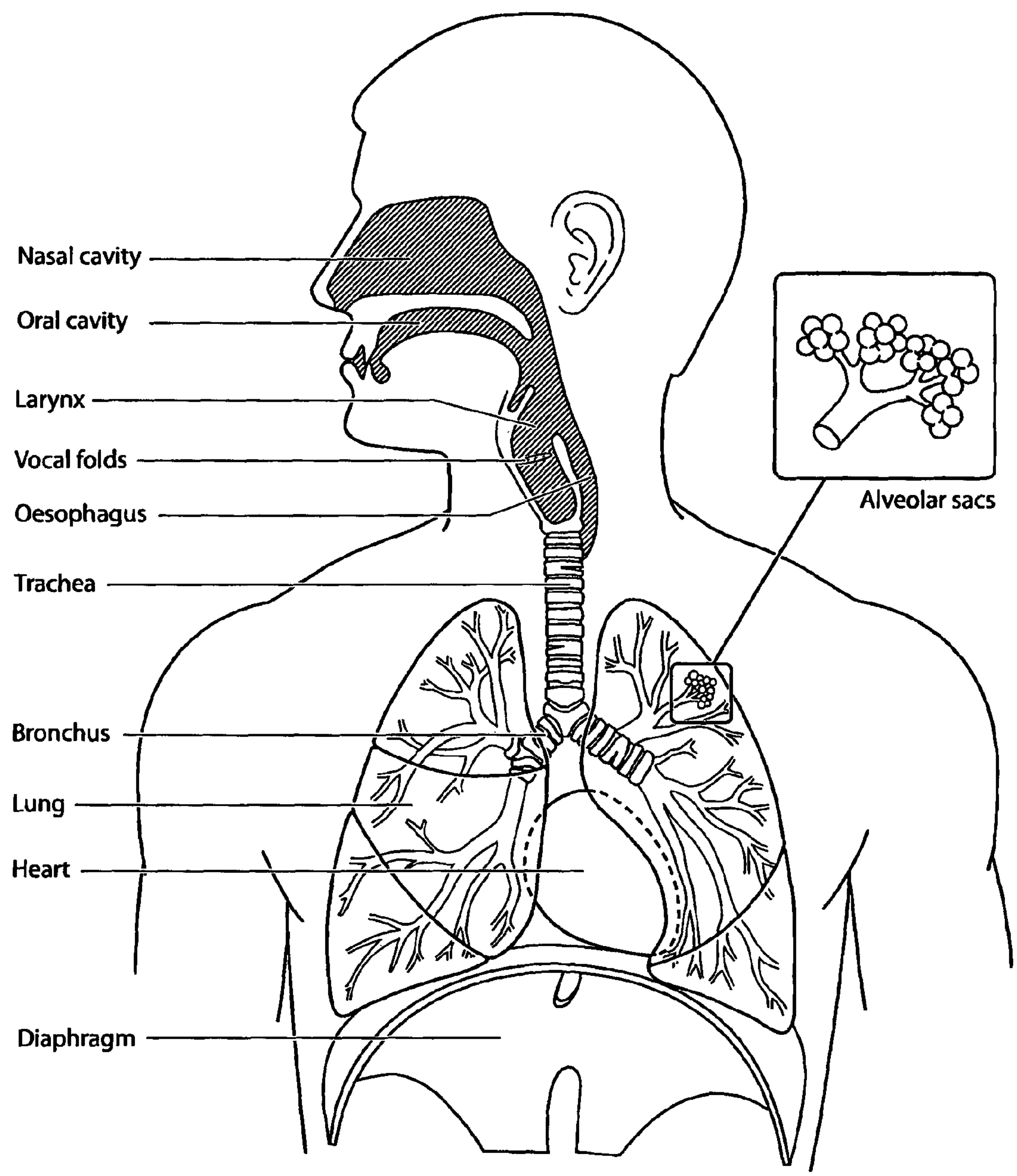
Figure 2B:
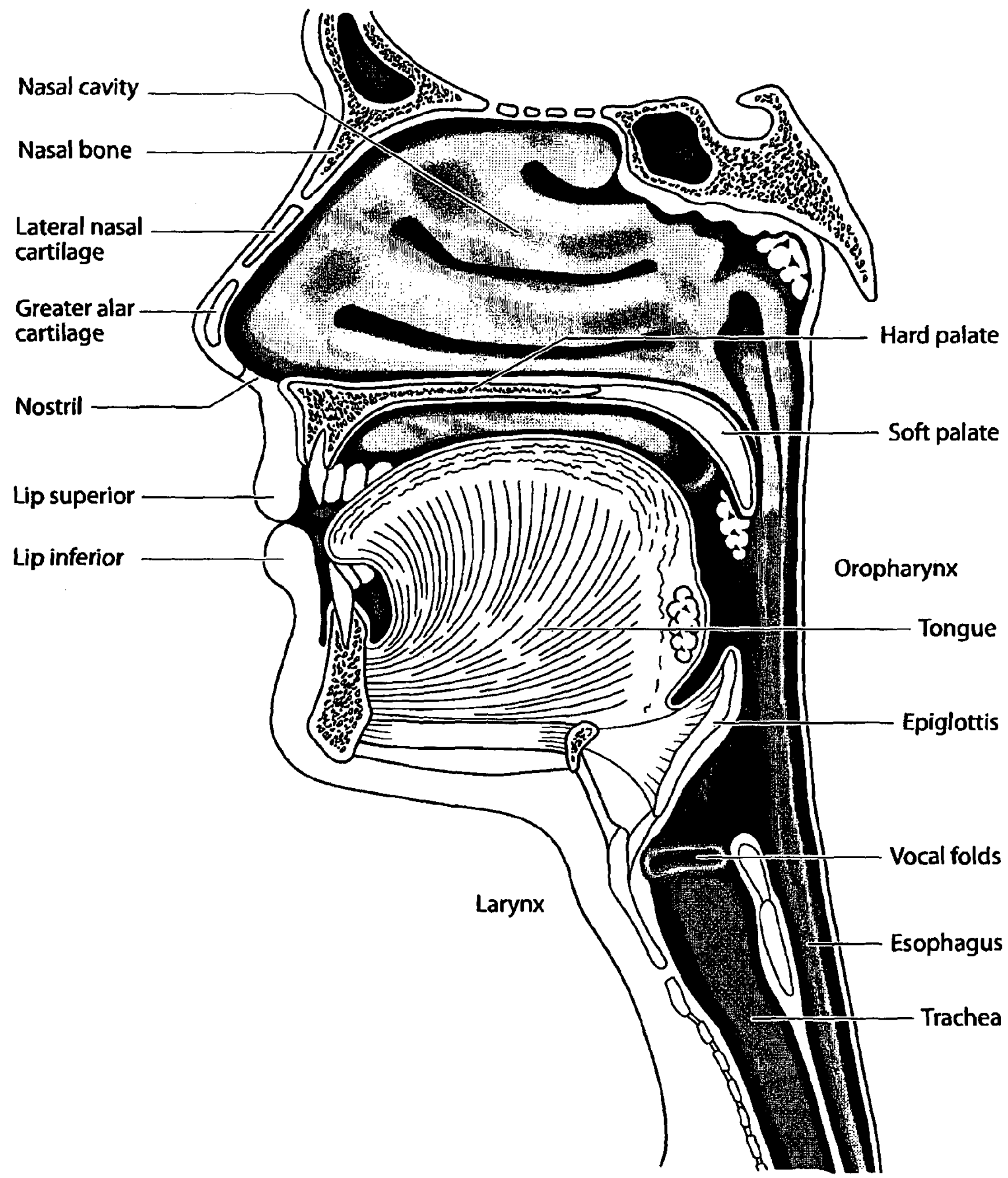
Figure 2C:
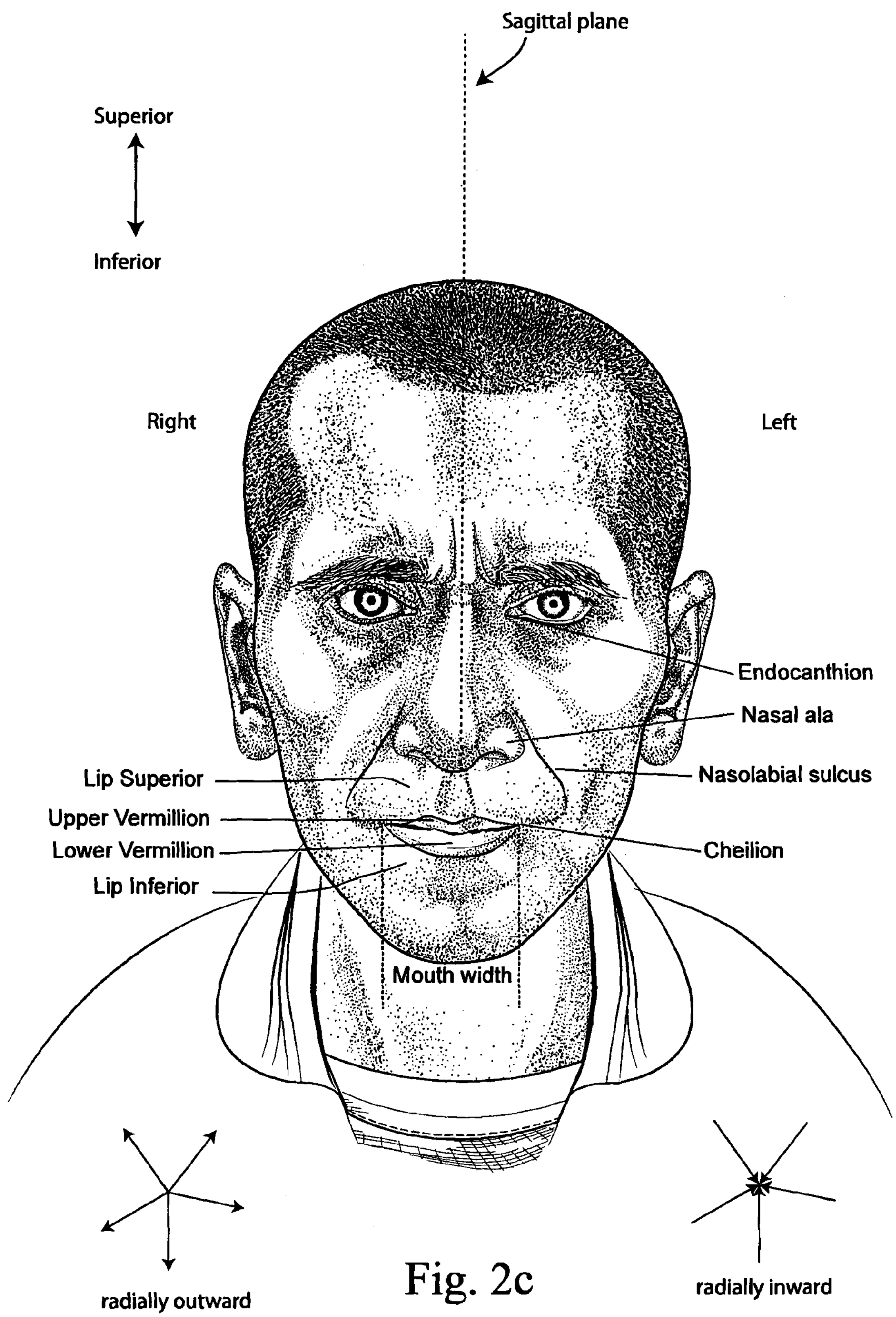
Figure 2D:
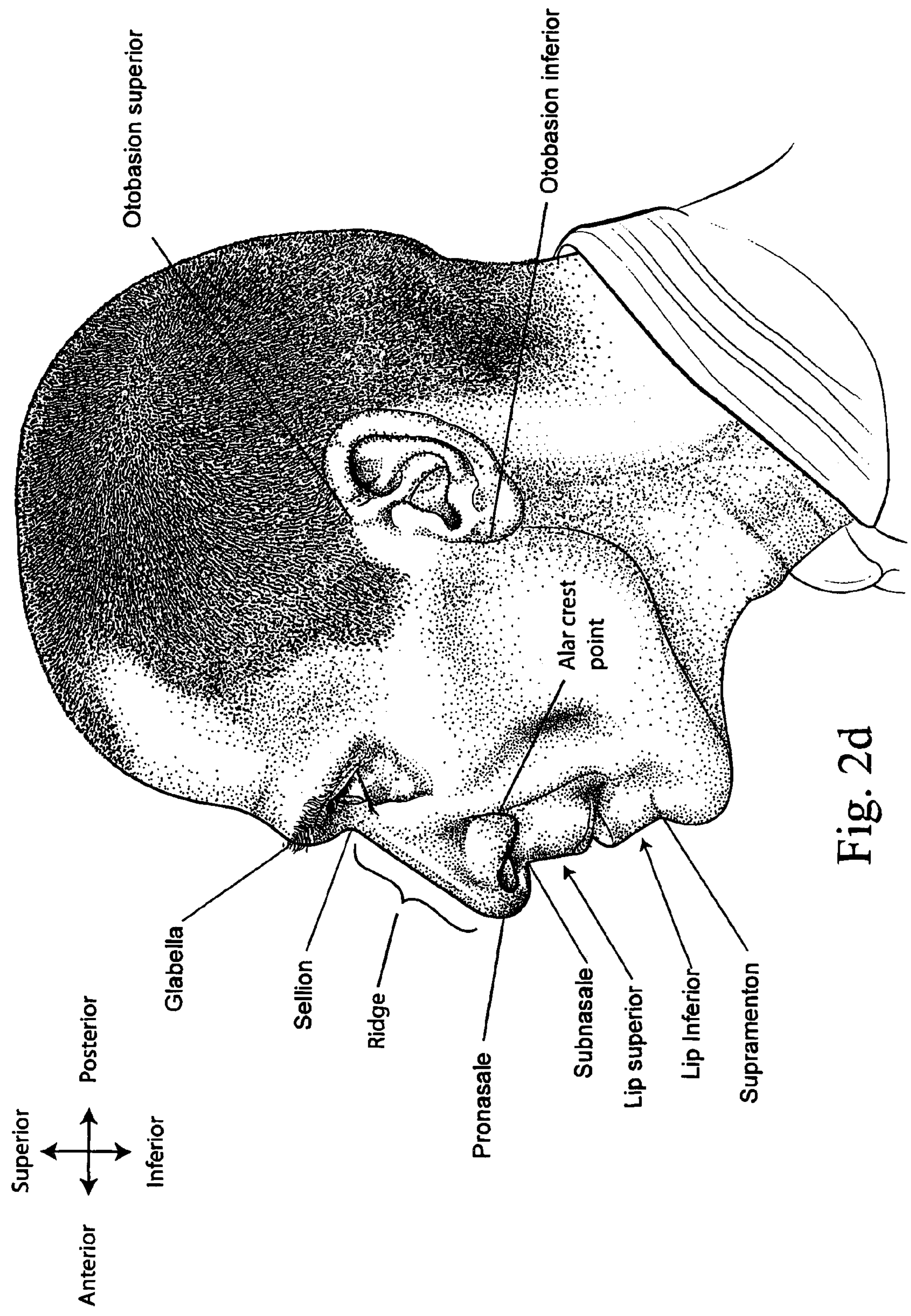
Figure 2E:
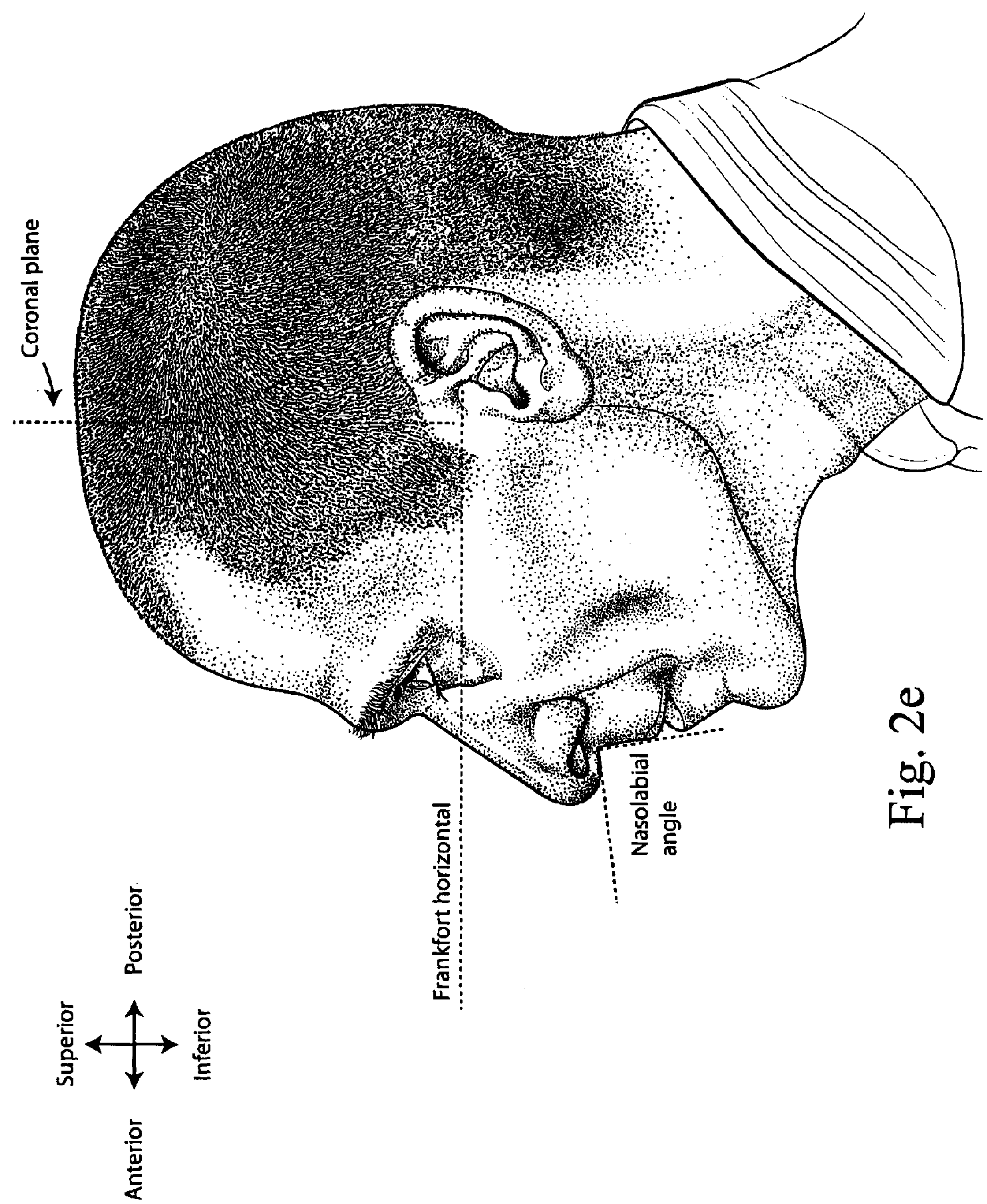
Figure 2F:
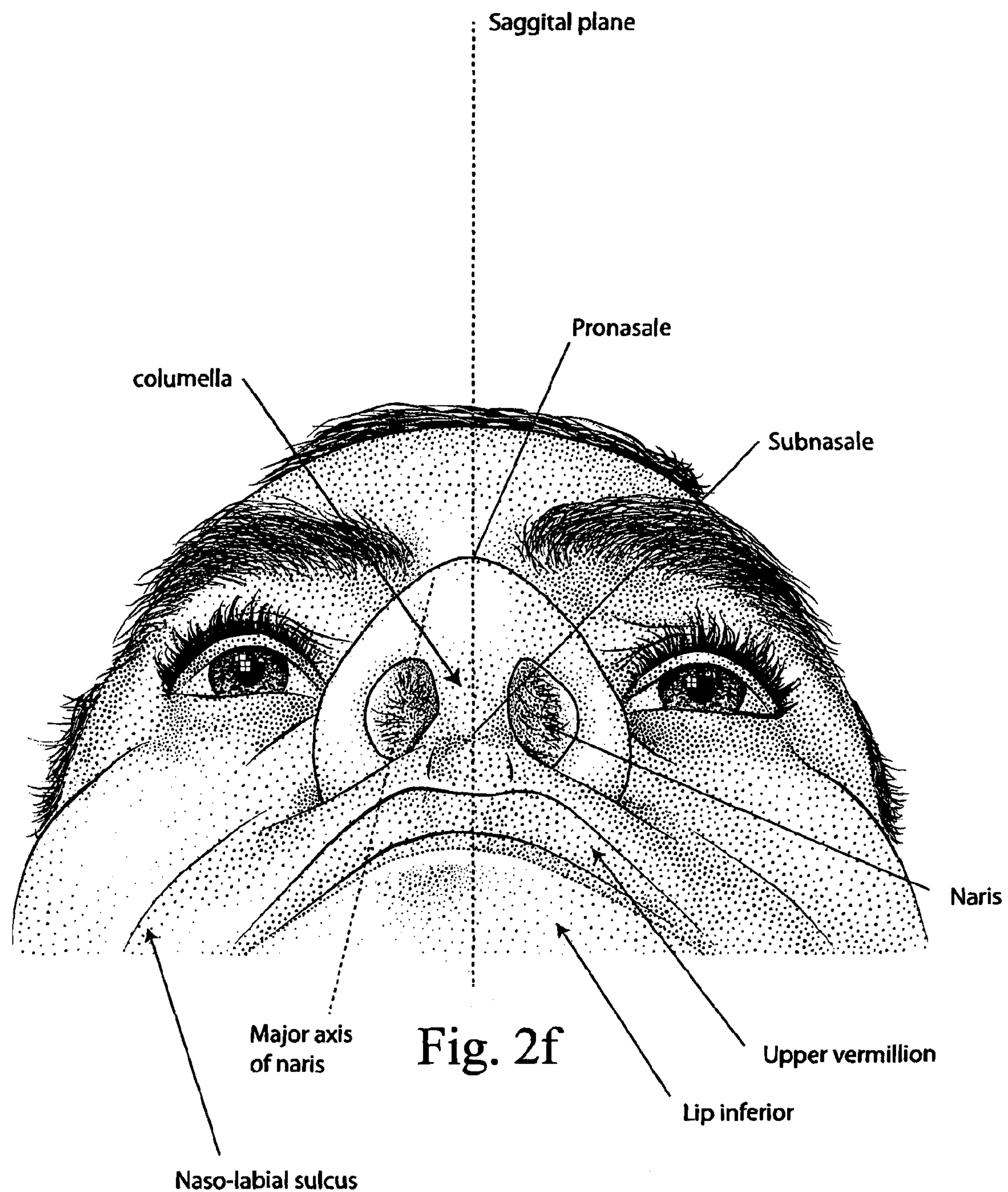
Figure 2I:
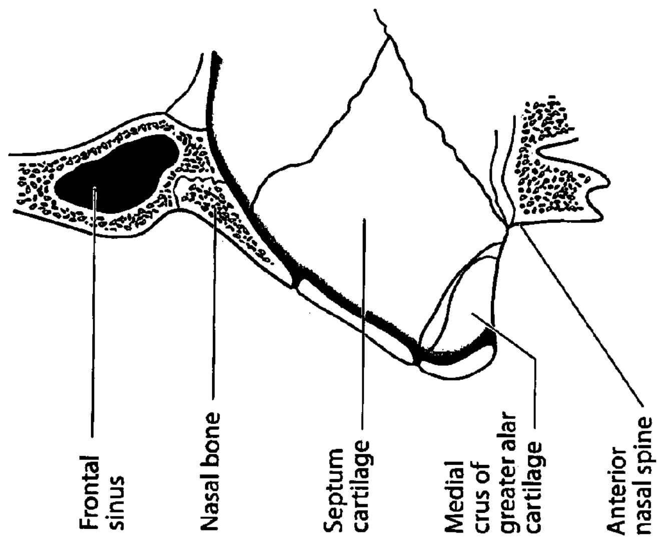
Figure 2H:
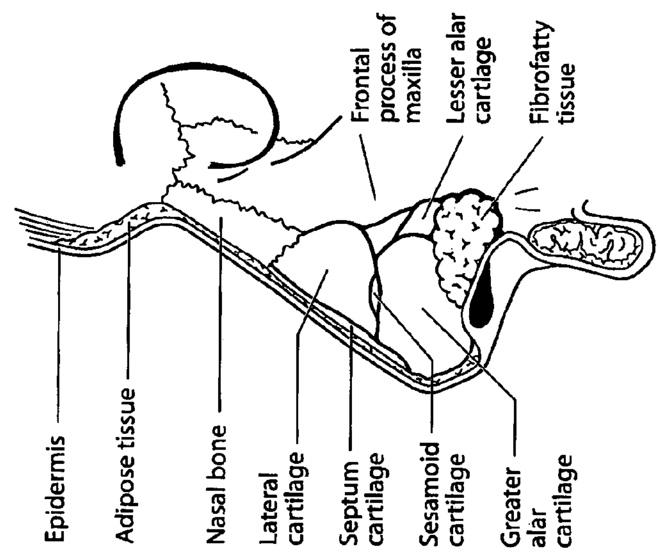
Figure 2G:
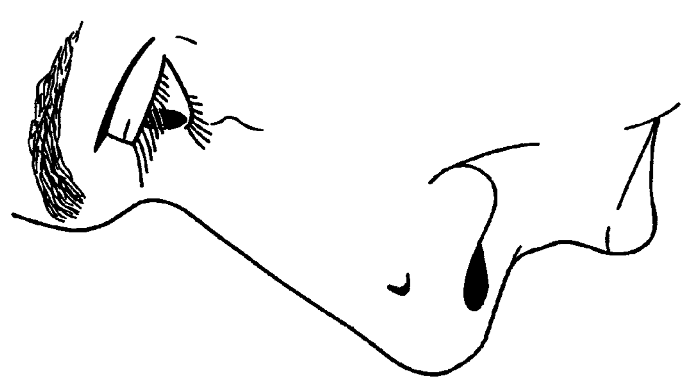
Figures 2J, 2K:
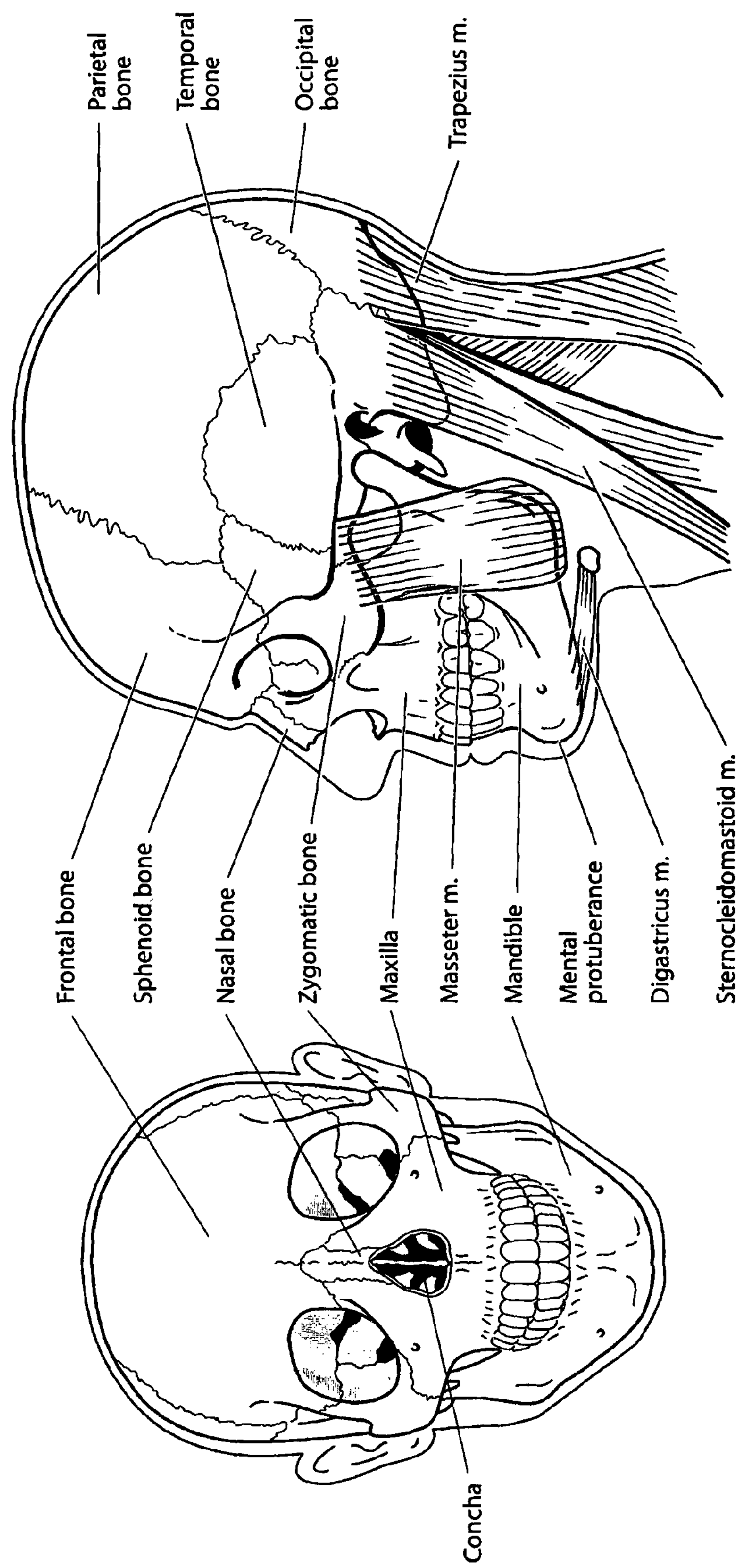
Figure 21:
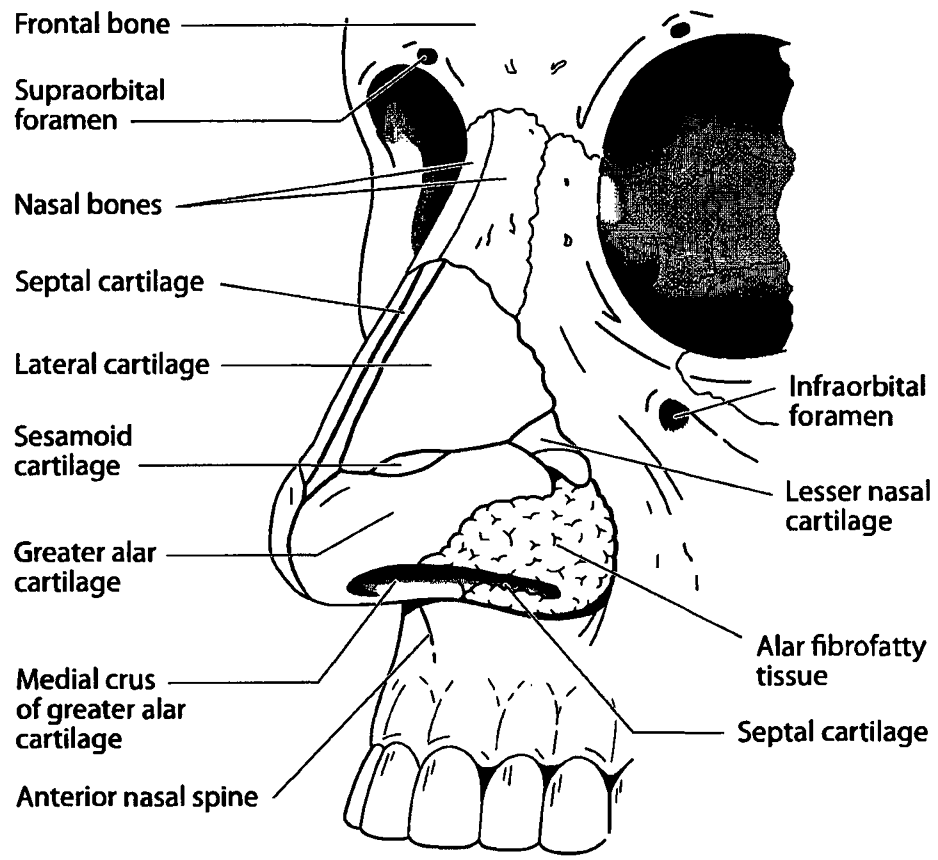
Figures 1, 3:
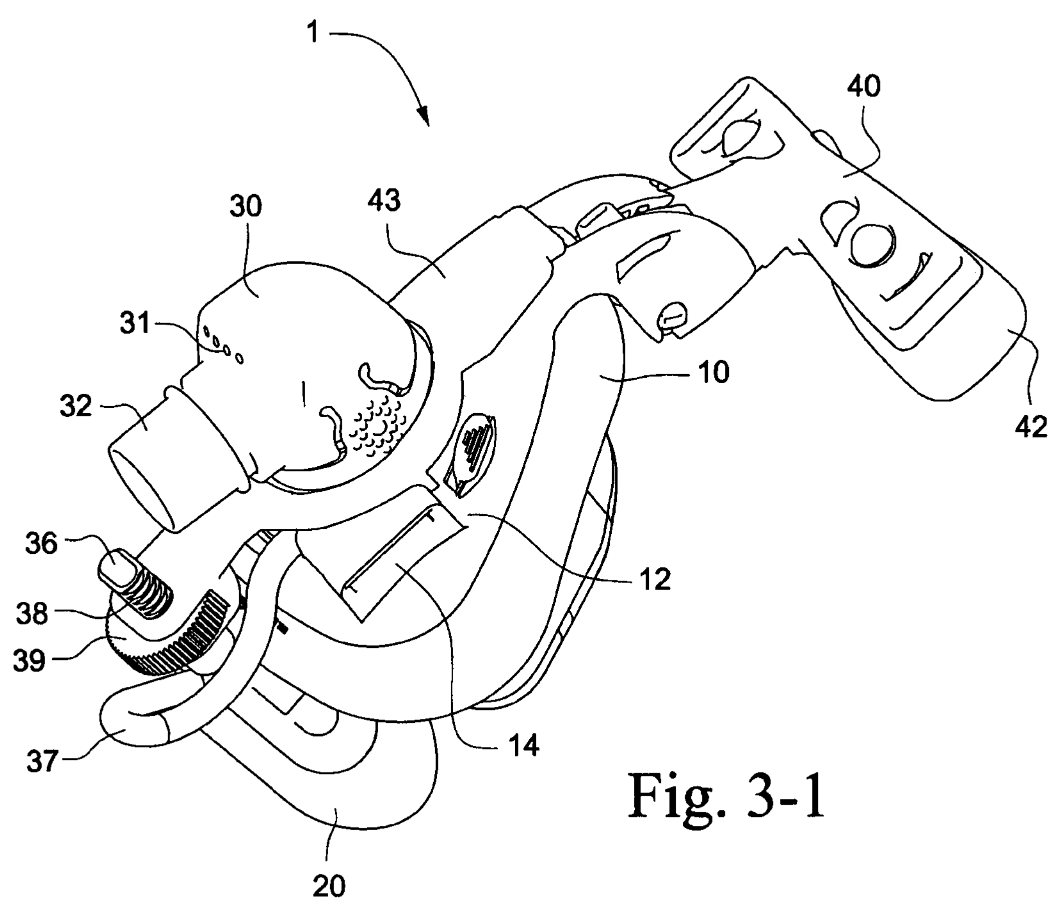
Figures 2, 3:
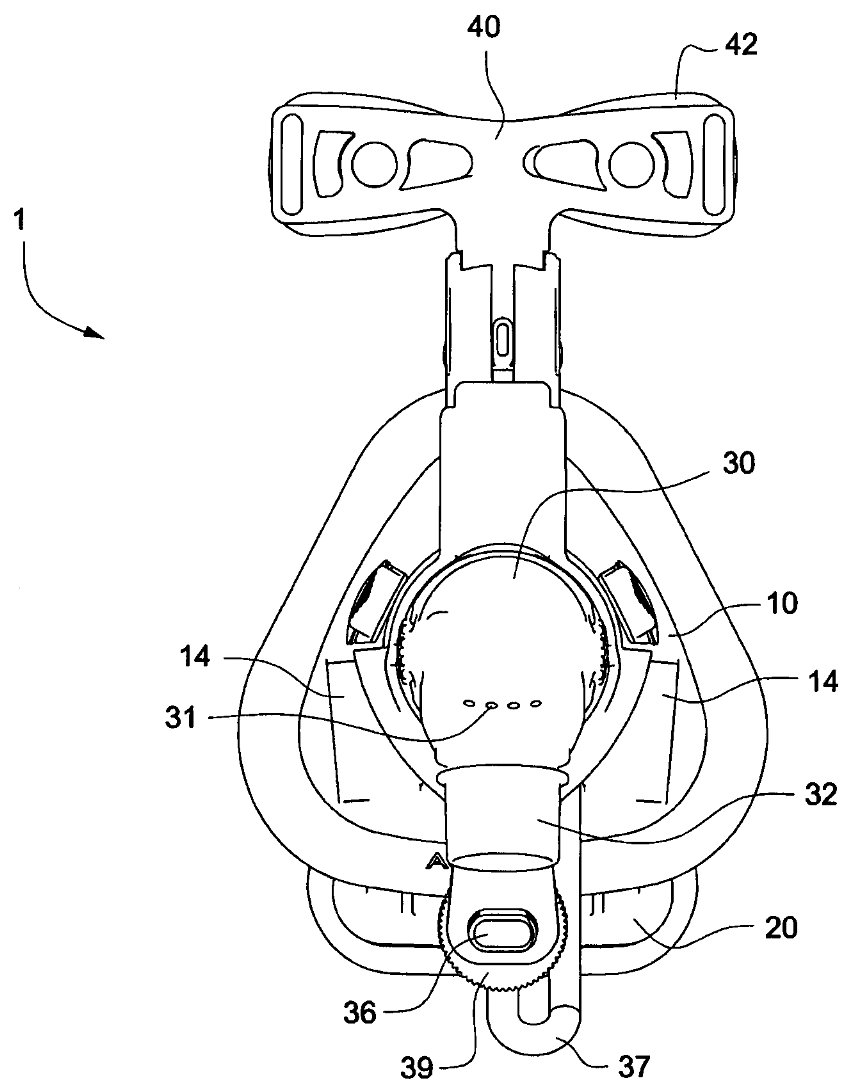
Figure 3:
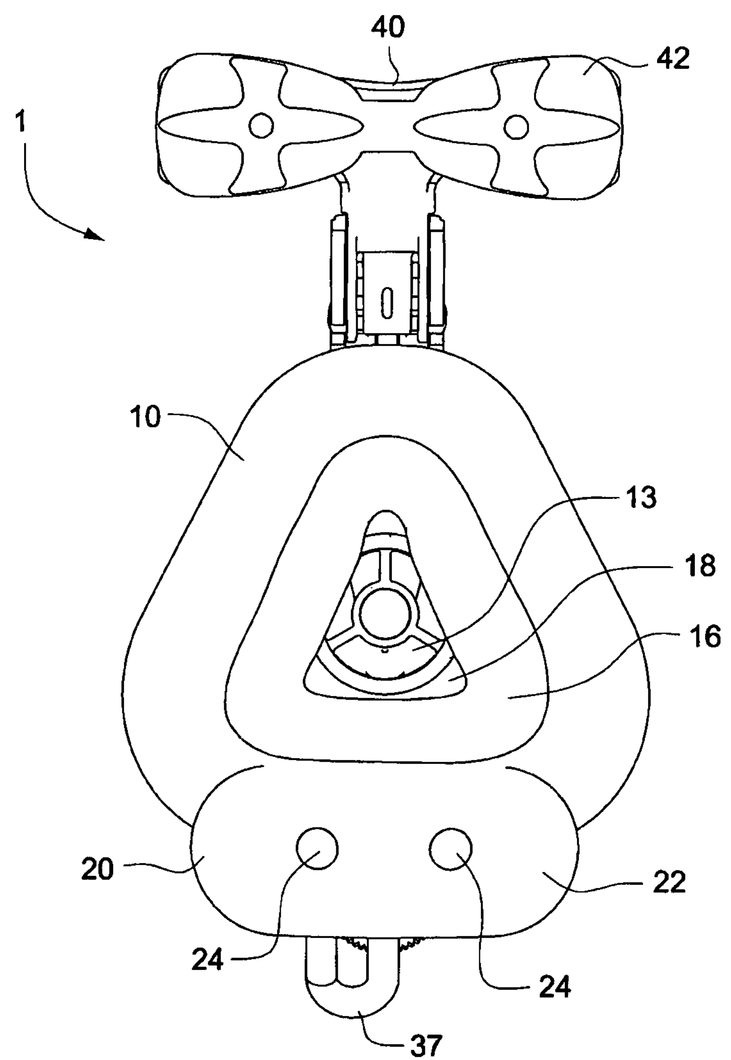
Figures 3, 4:
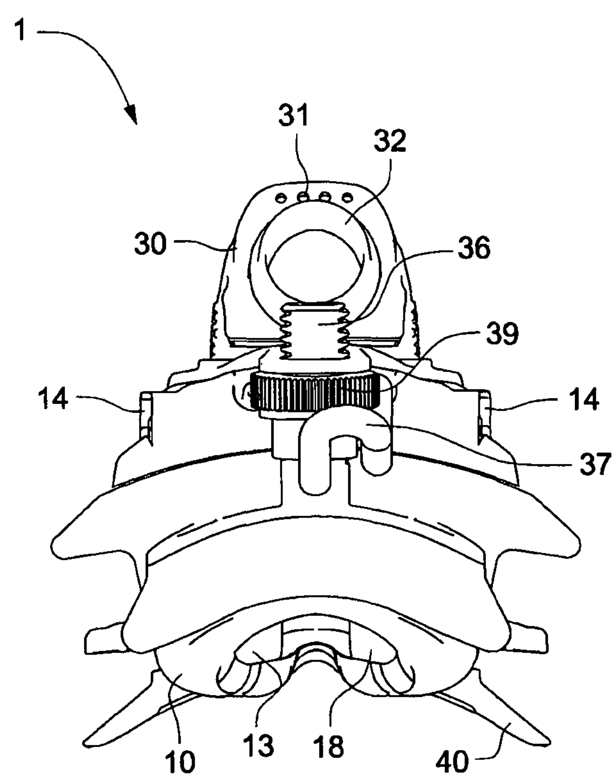
Figures 3, 4, 5:
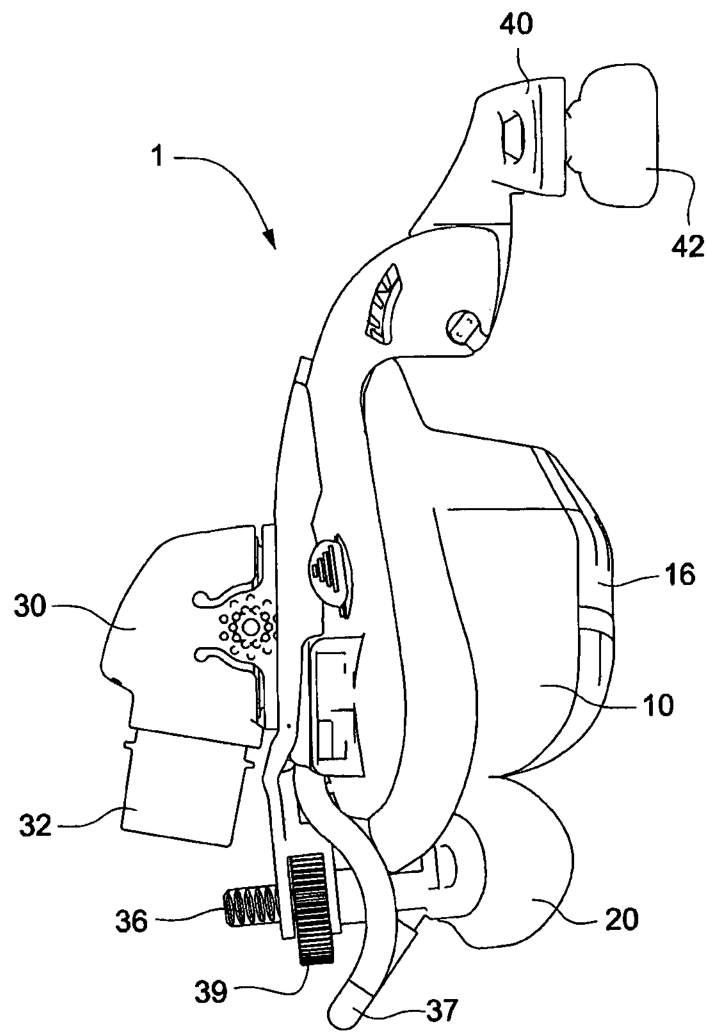
Figures 3, 4, 5, 6:
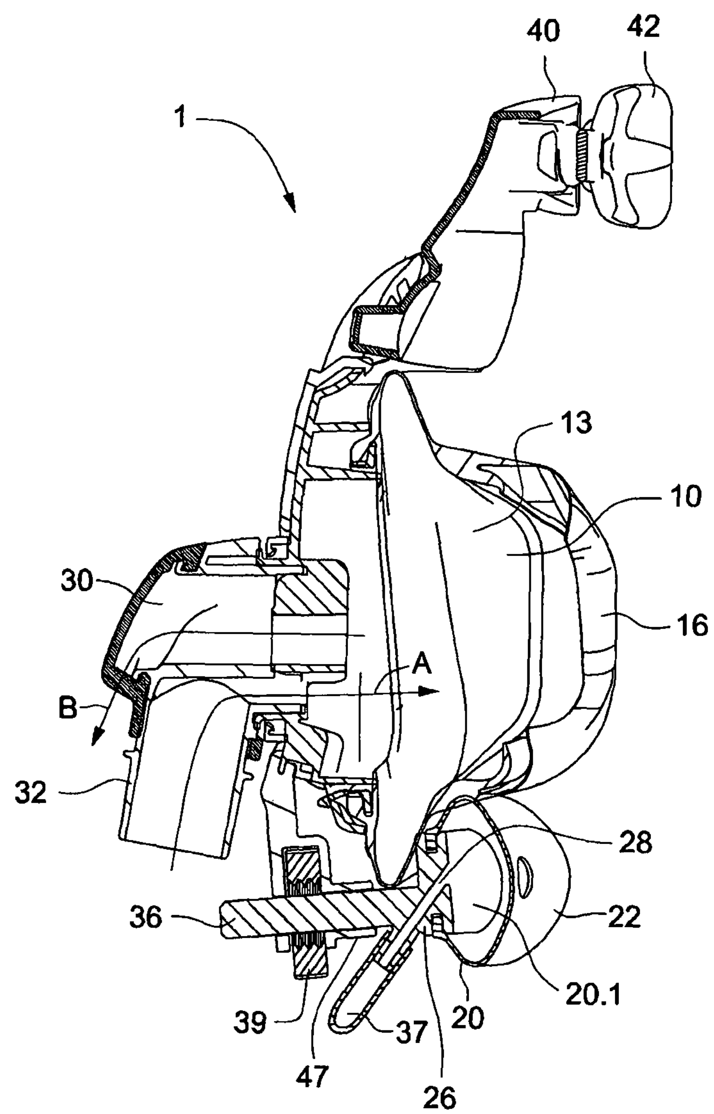
Figures 3, 4, 5, 6, 7:
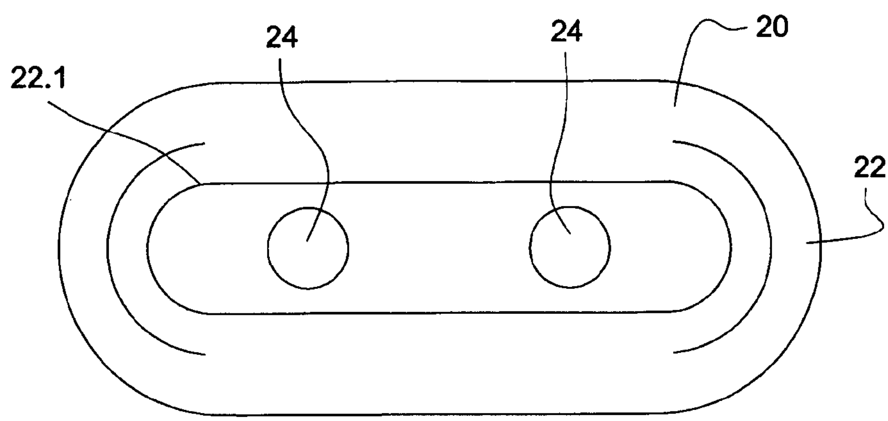
Figures 3, 4, 5, 6, 7, 8:
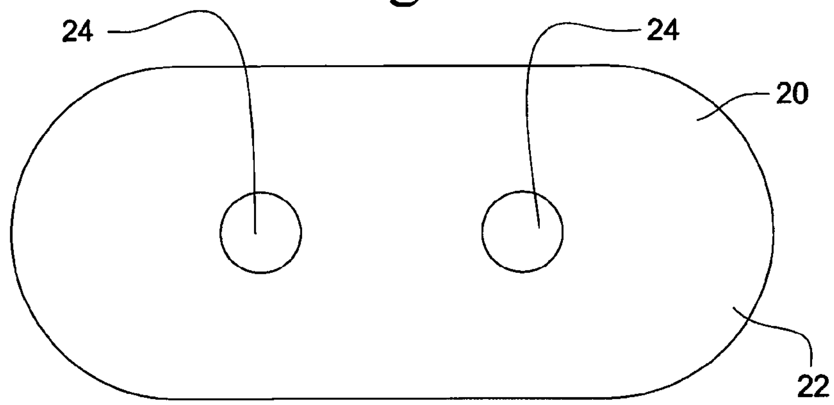
Figures 3, 4, 5, 6, 7, 8, 9:
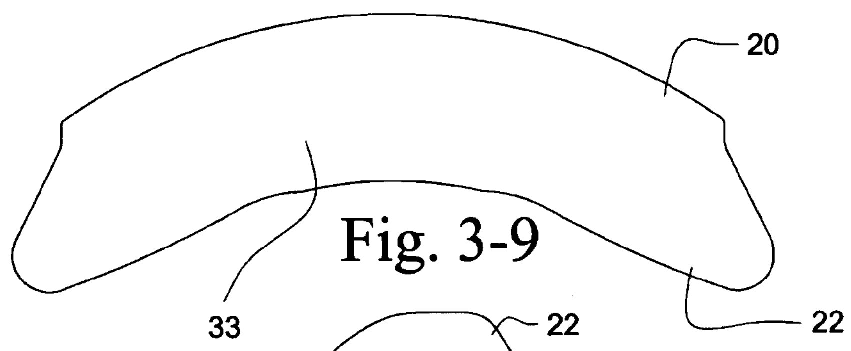
Figures 3, 4, 5, 6, 7, 8, 9, 10:
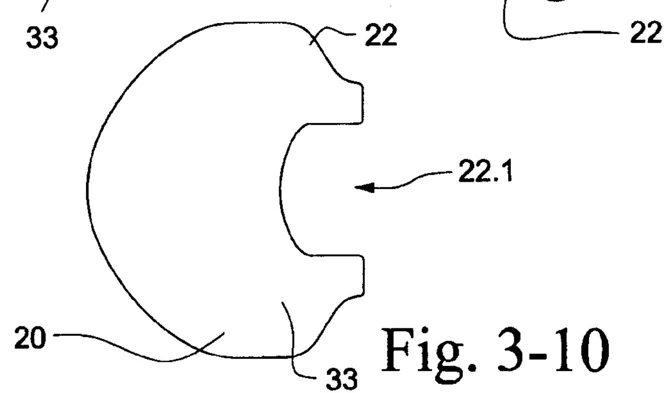
Figures 3, 4, 5, 6, 7, 8, 9, 10, 11:
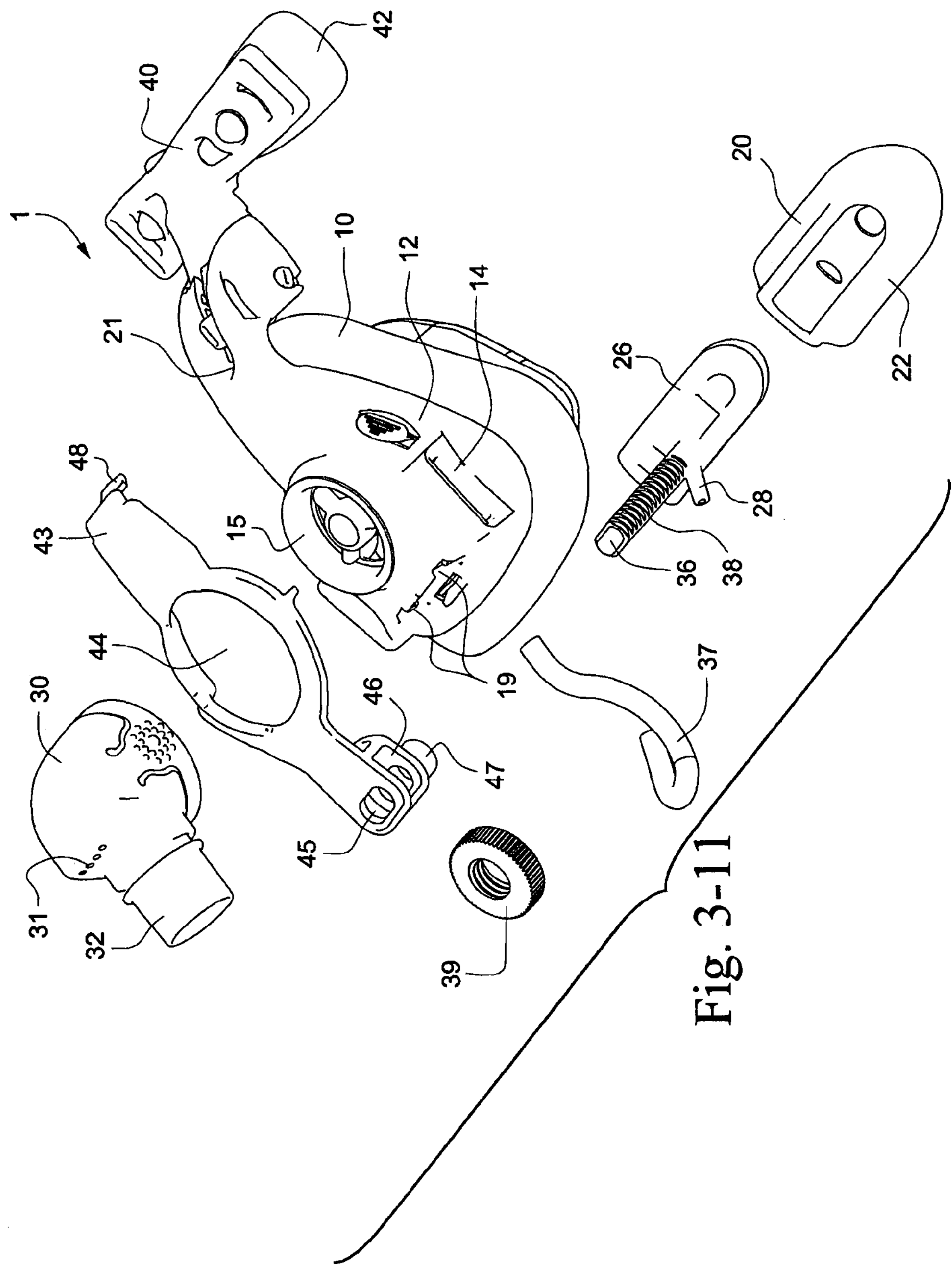
Figures 3, 4, 5, 6, 7, 8, 9, 10, 11, 12:
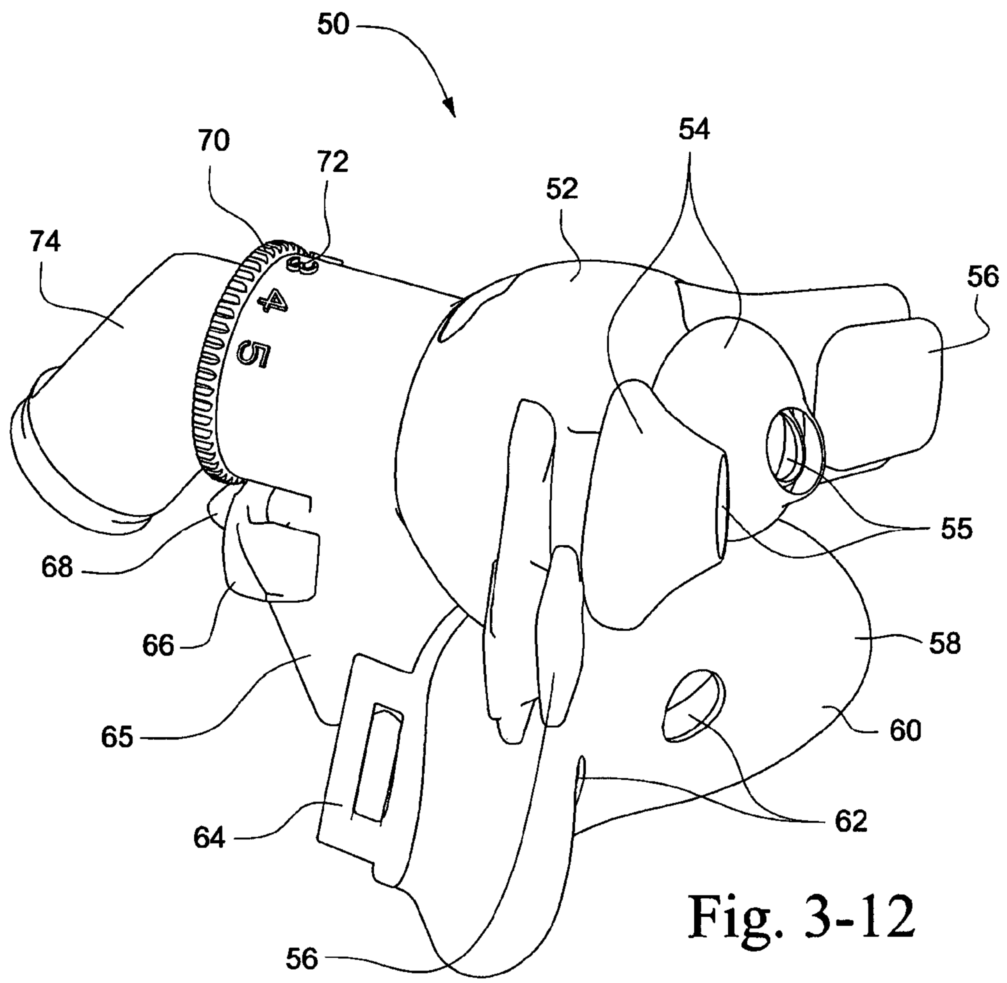
Figures 3, 4, 5, 6, 7, 8, 9, 10, 11, 12, 13:
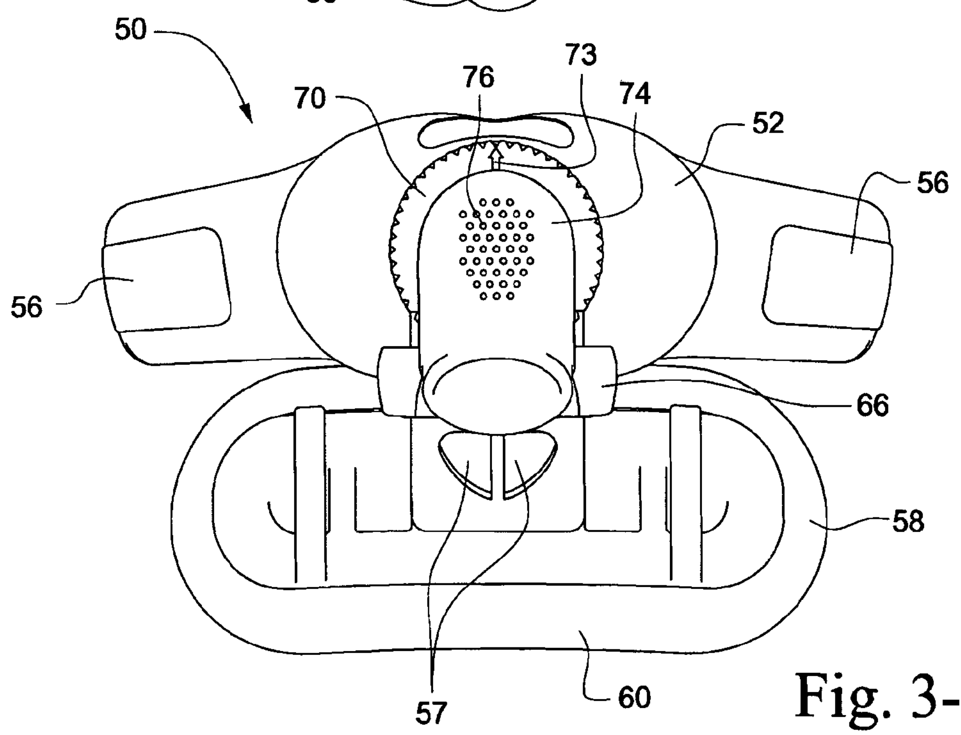
Figures 3, 4, 5, 6, 7, 8, 9, 10, 11, 12, 13, 14:
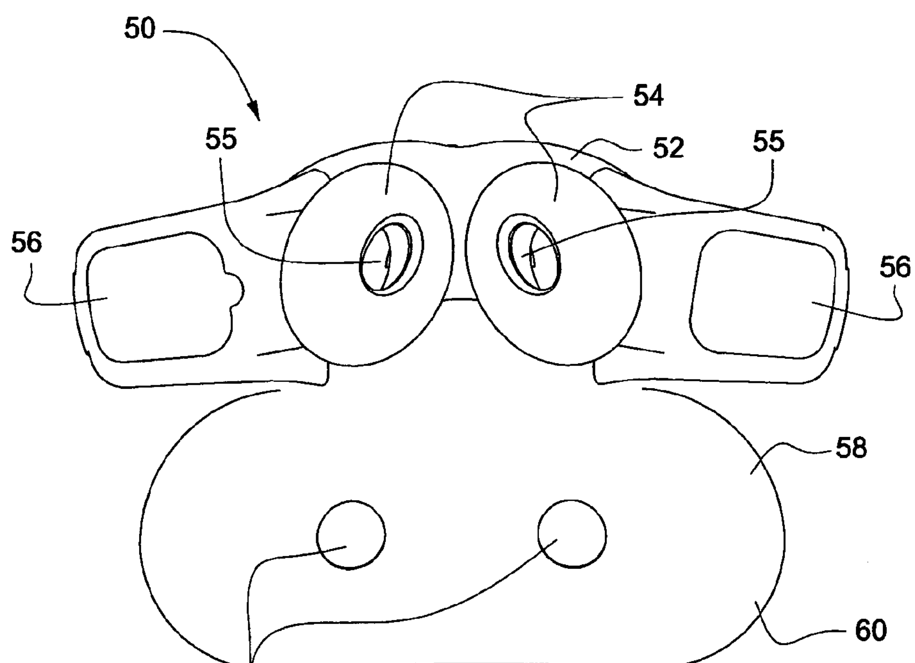
Figures 3, 4, 5, 6, 7, 8, 9, 10, 11, 12, 13, 14, 15:
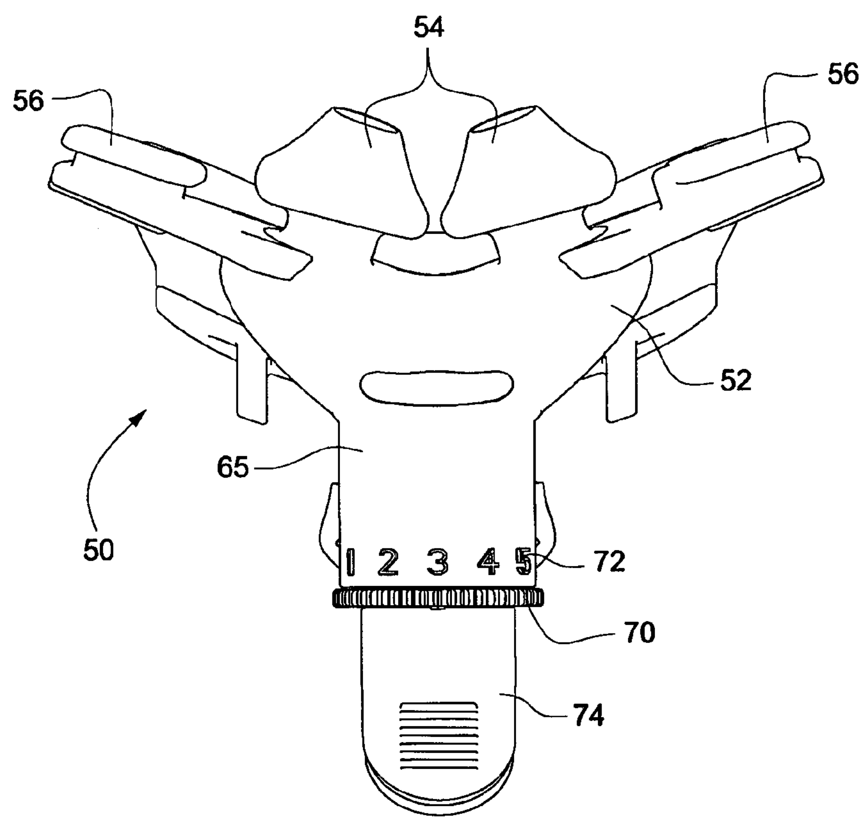
Figures 3, 4, 5, 6, 7, 8, 9, 10, 11, 12, 13, 14, 15, 16:
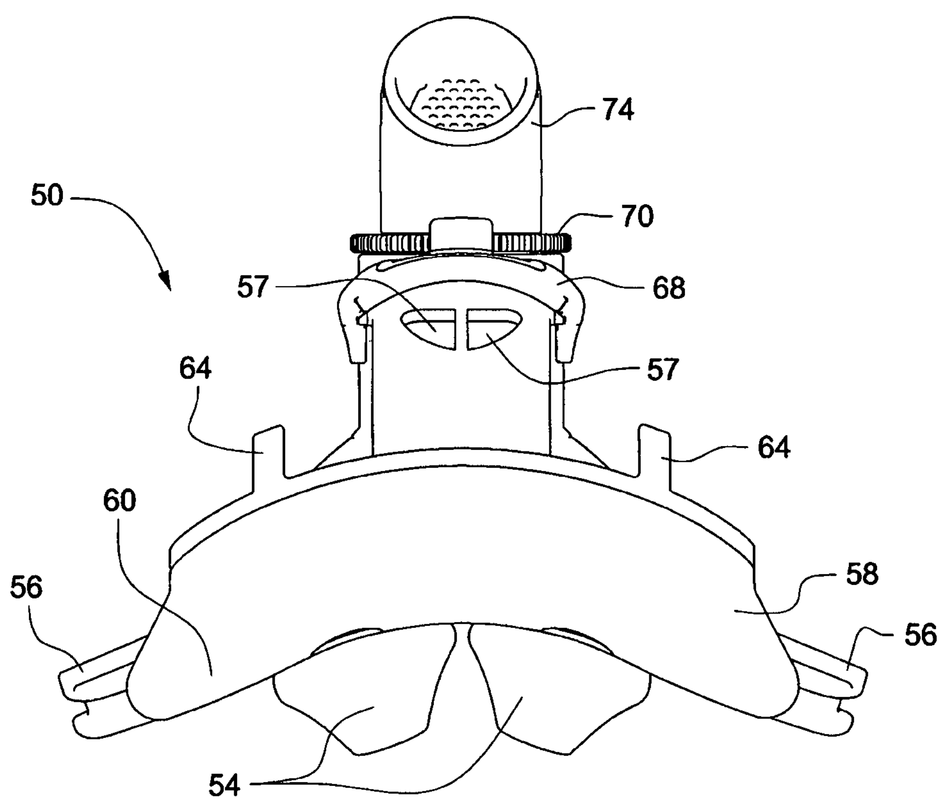
Figures 3, 4, 5, 6, 7, 8, 9, 10, 11, 12, 13, 14, 15, 16, 17:
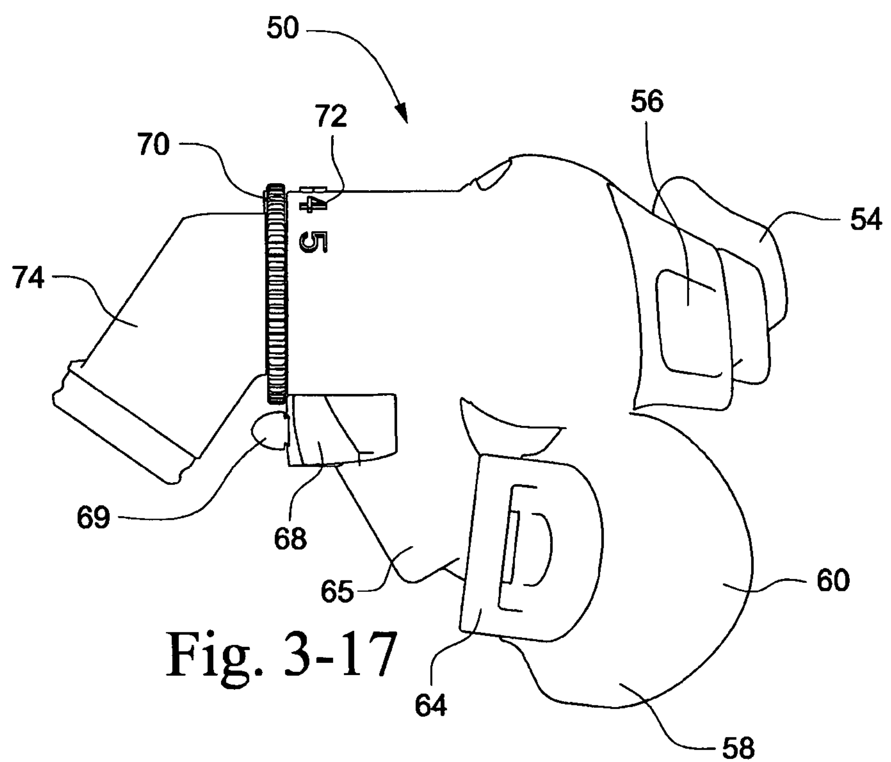
Figures 3, 4, 5, 6, 7, 8, 9, 10, 11, 12, 13, 14, 15, 16, 17, 18:
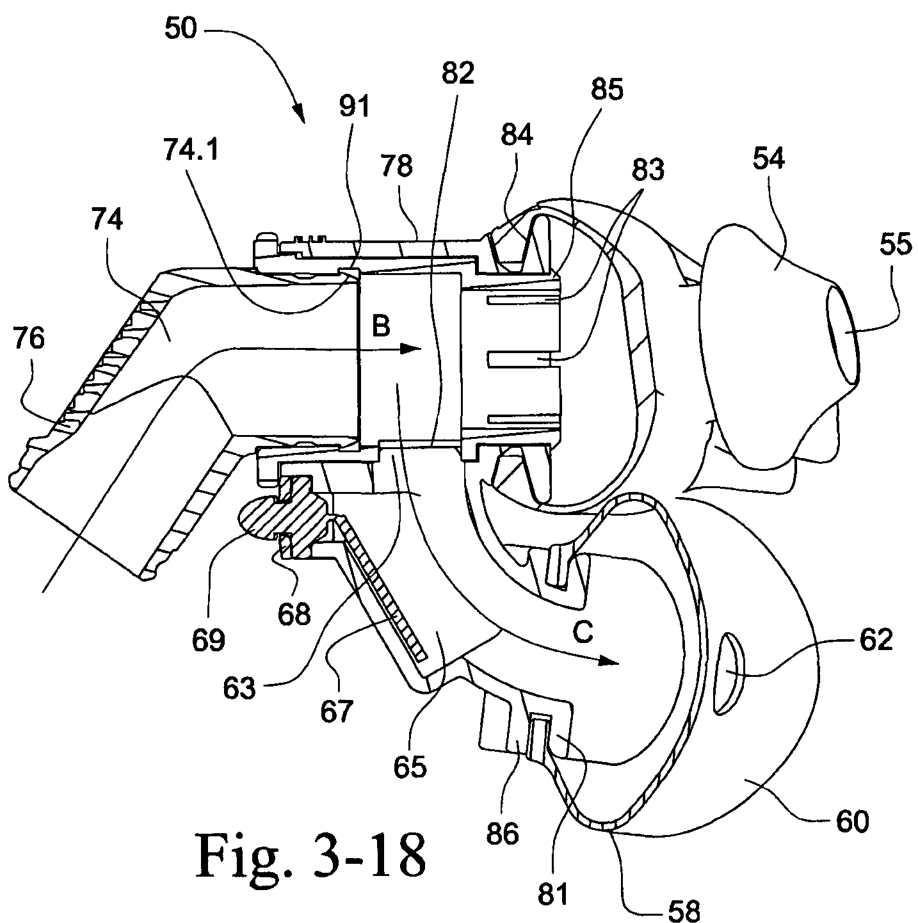
Figures 3, 4, 5, 6, 7, 8, 9, 10, 11, 12, 13, 14, 15, 16, 17, 18, 19:
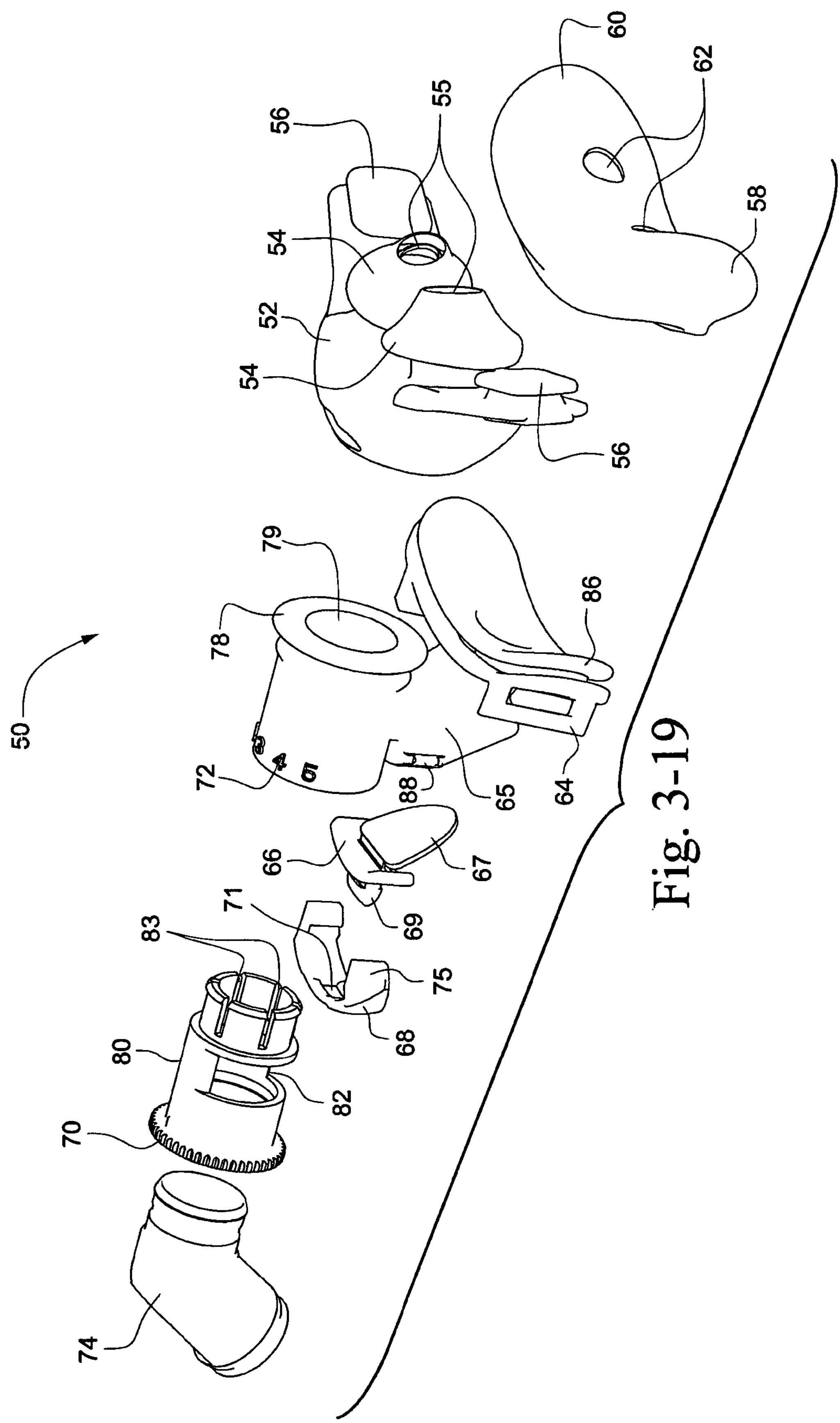
Figures 3, 4, 5, 6, 7, 8, 9, 10, 11, 12, 13, 14, 15, 16, 17, 18, 19, 20:
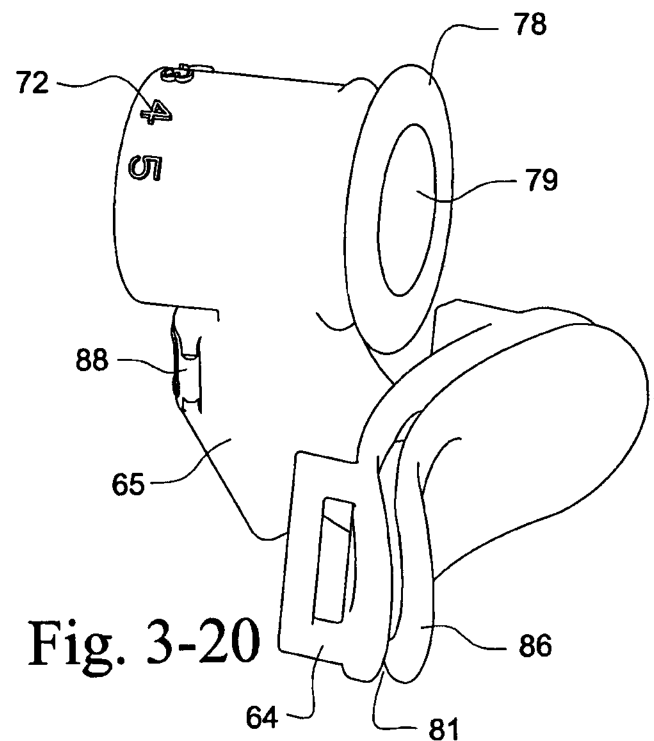
Figures 3, 4, 5, 6, 7, 8, 9, 10, 11, 12, 13, 14, 15, 16, 17, 18, 19, 20, 21:
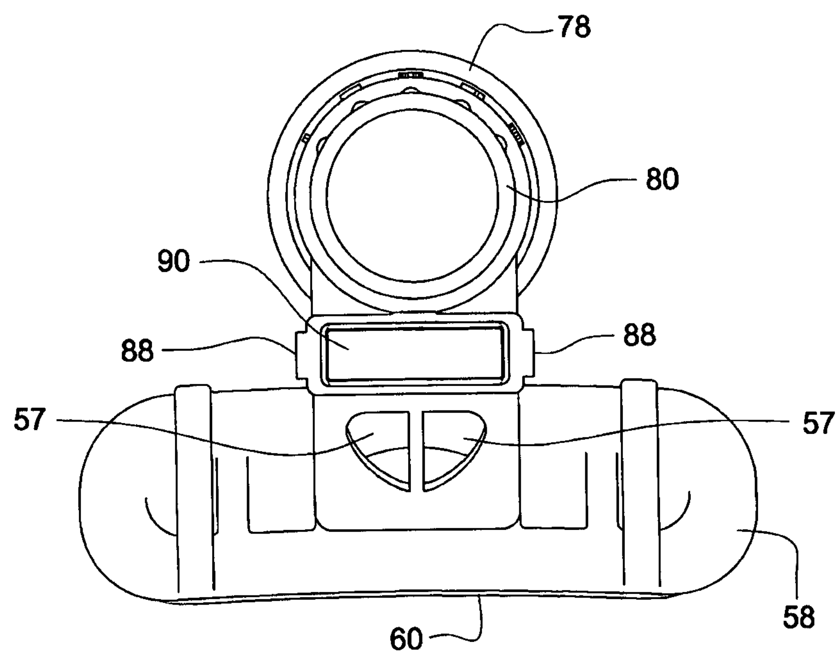
Figures 3, 4, 5, 6, 7, 8, 9, 10, 11, 12, 13, 14, 15, 16, 17, 18, 19, 20, 21, 22:
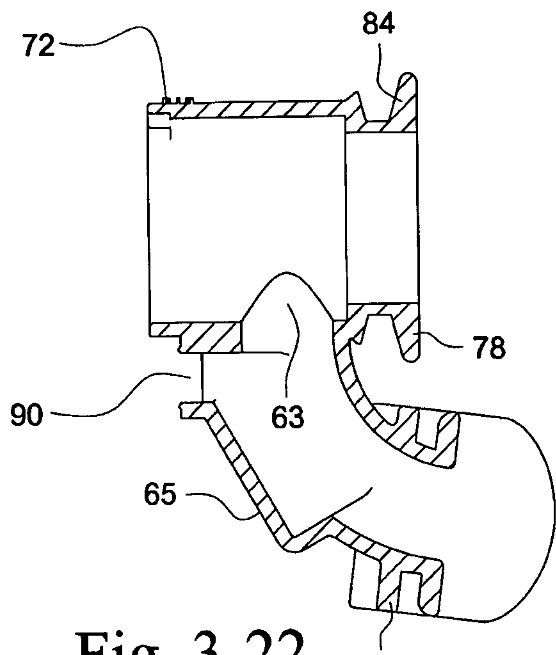
Figures 3, 4, 5, 6, 7, 8, 9, 10, 11, 12, 13, 14, 15, 16, 17, 18, 19, 20, 21, 22, 23:
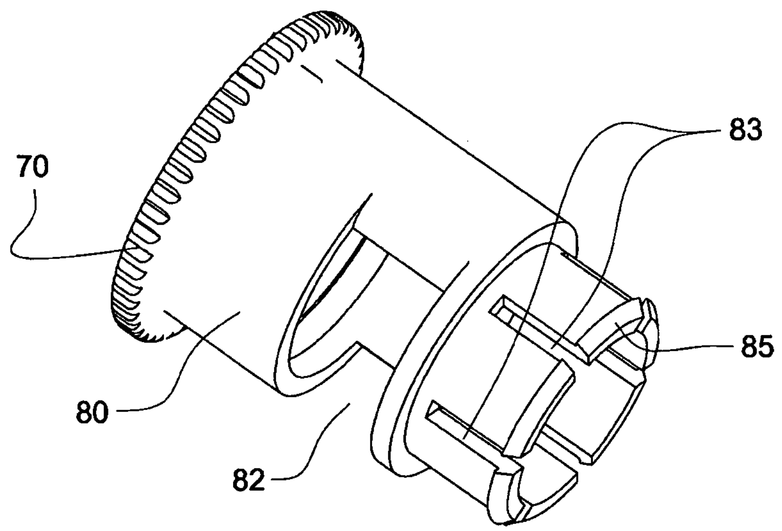
Figures 3, 4, 5, 6, 7, 8, 9, 10, 11, 12, 13, 14, 15, 16, 17, 18, 19, 20, 21, 22, 23, 24:
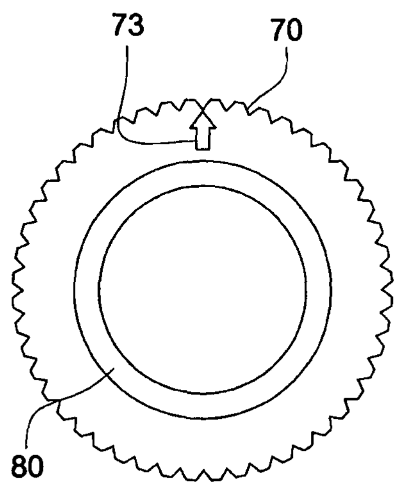
Figures 3, 4, 5, 6, 7, 8, 9, 10, 11, 12, 13, 14, 15, 16, 17, 18, 19, 20, 21, 22, 23, 24, 25:
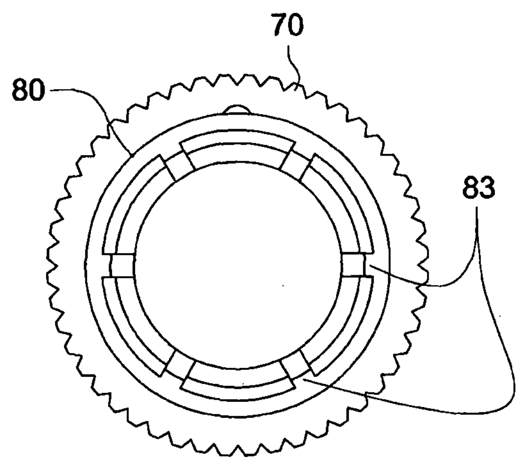
Figures 3, 4, 5, 6, 7, 8, 9, 10, 11, 12, 13, 14, 15, 16, 17, 18, 19, 20, 21, 22, 23, 24, 25, 26:
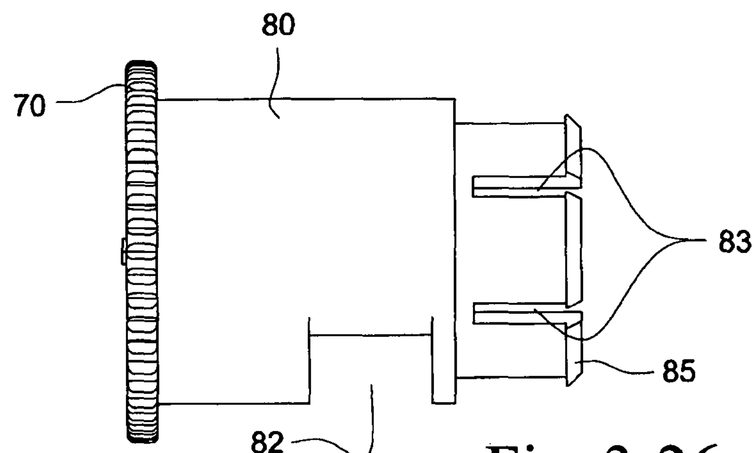
Figures 3, 4, 5, 6, 7, 8, 9, 10, 11, 12, 13, 14, 15, 16, 17, 18, 19, 20, 21, 22, 23, 24, 25, 26, 27:
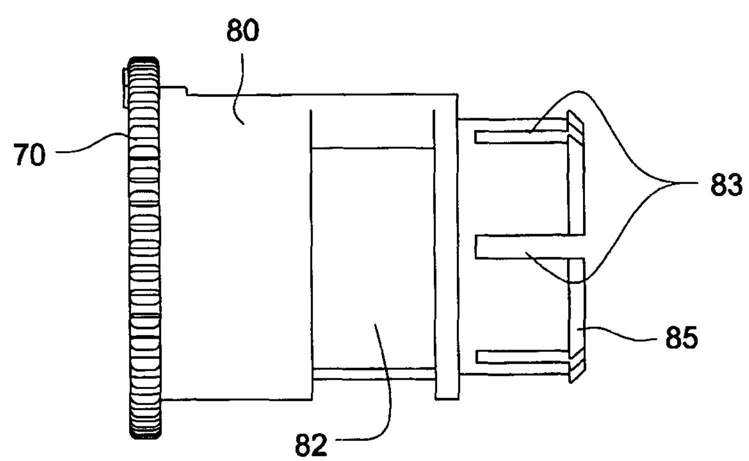
Figures 3, 4, 5, 6, 7, 8, 9, 10, 11, 12, 13, 14, 15, 16, 17, 18, 19, 20, 21, 22, 23, 24, 25, 26, 27, 28:
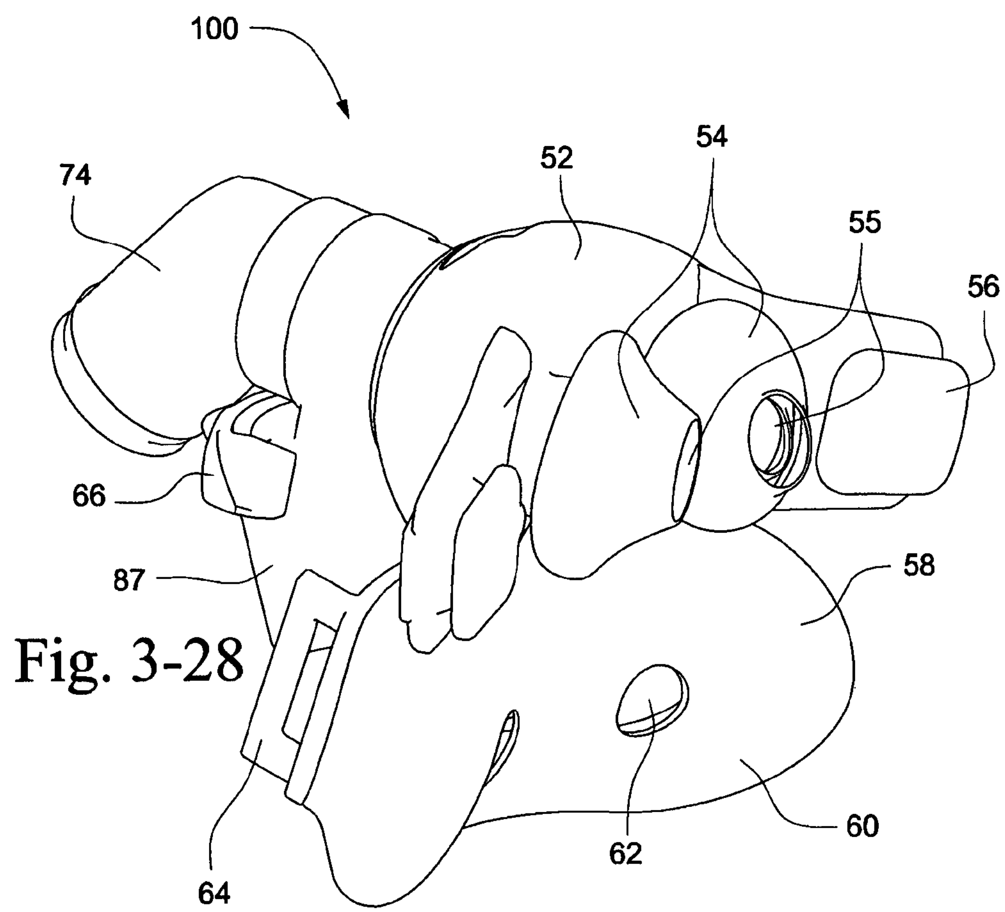
Figures 3, 4, 5, 6, 7, 8, 9, 10, 11, 12, 13, 14, 15, 16, 17, 18, 19, 20, 21, 22, 23, 24, 25, 26, 27, 28, 29:
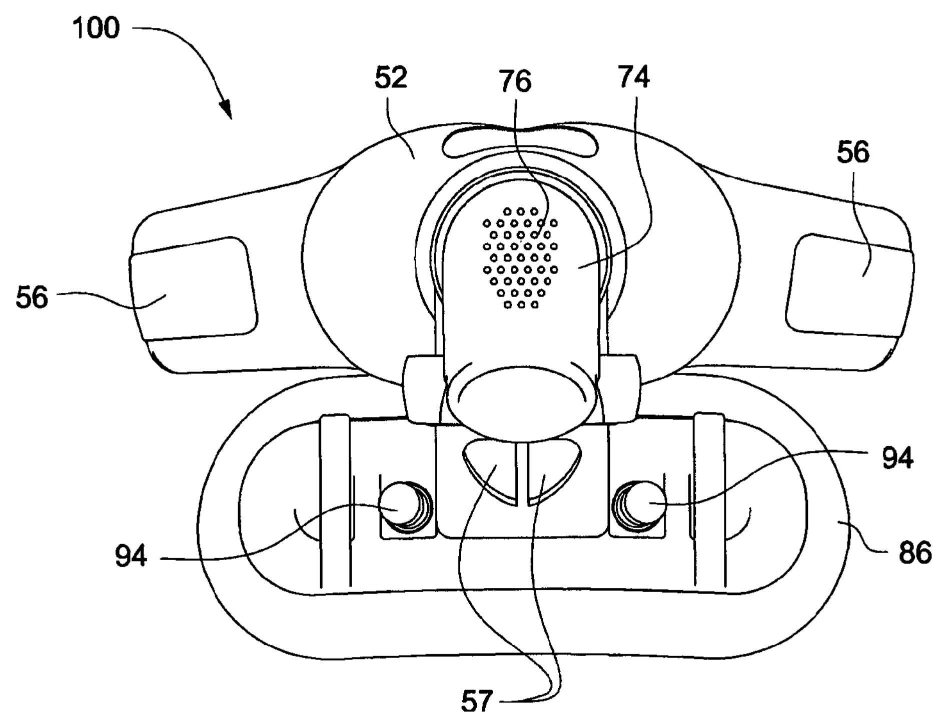
Figures 3, 4, 5, 6, 7, 8, 9, 10, 11, 12, 13, 14, 15, 16, 17, 18, 19, 20, 21, 22, 23, 24, 25, 26, 27, 28, 29, 30:
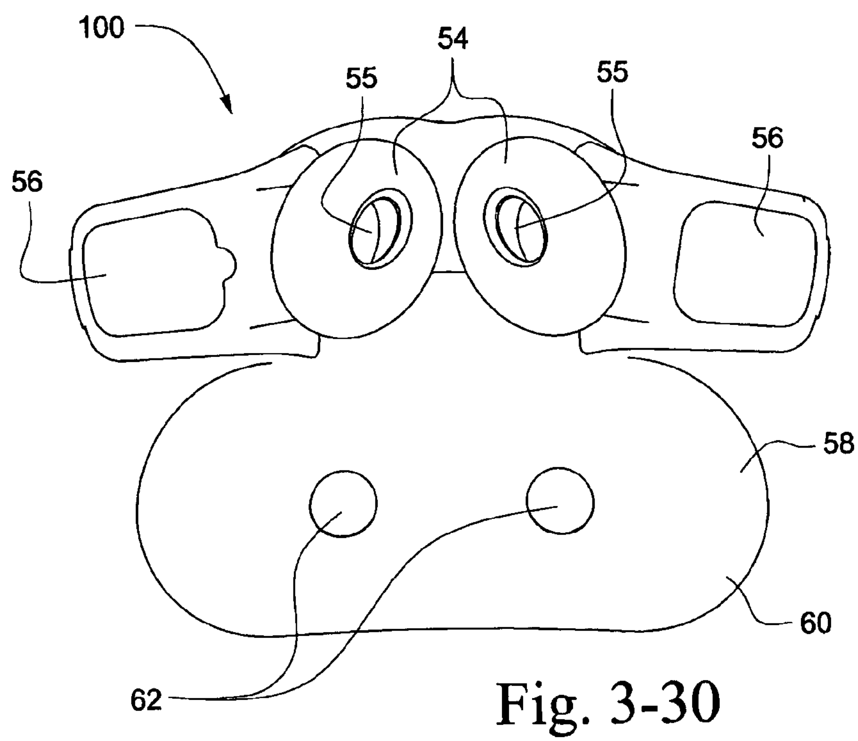
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31:
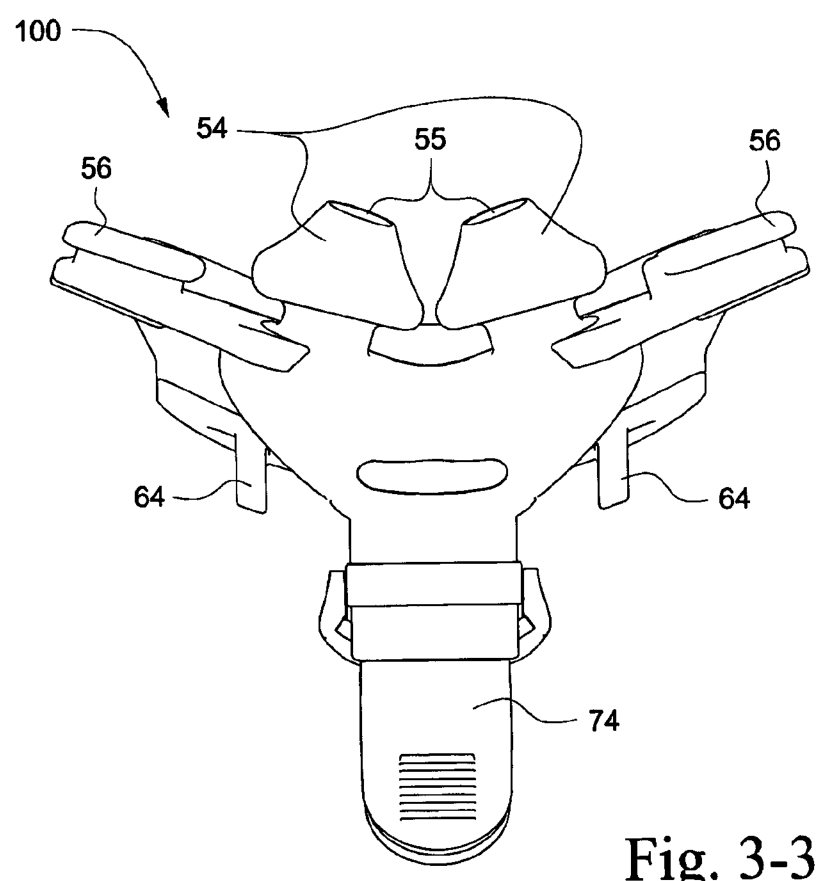
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
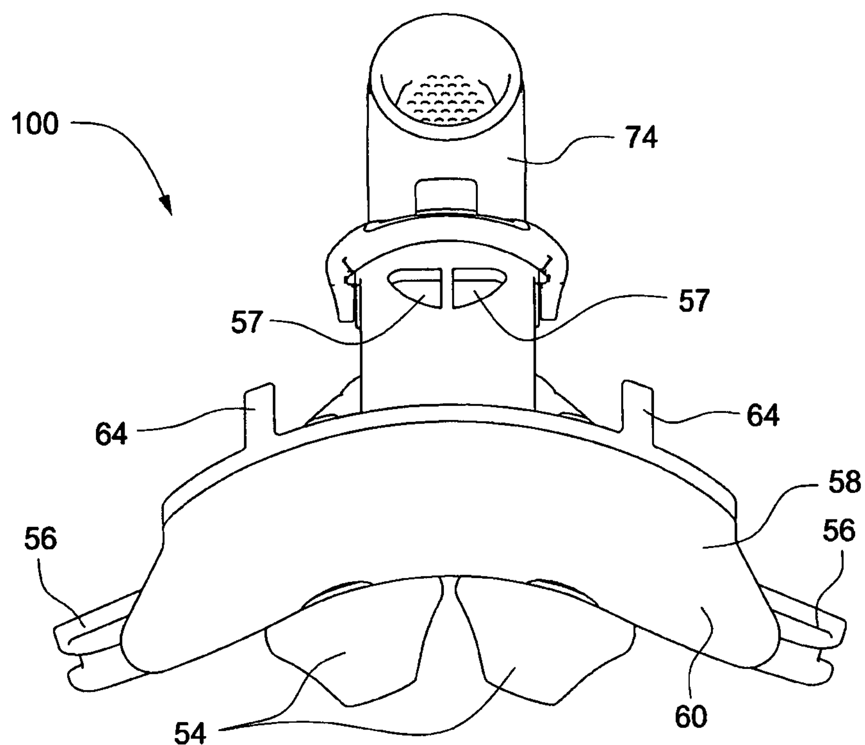
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
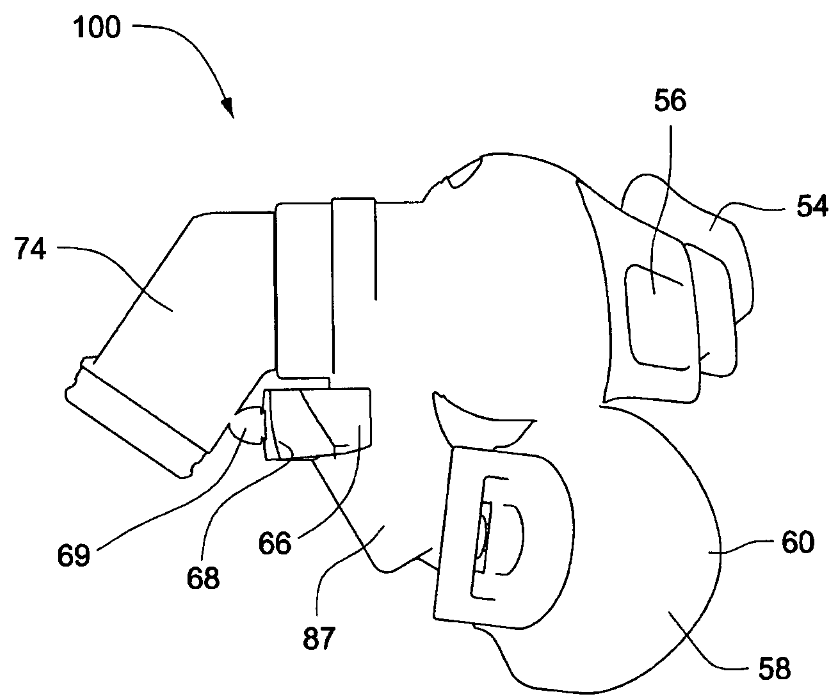
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
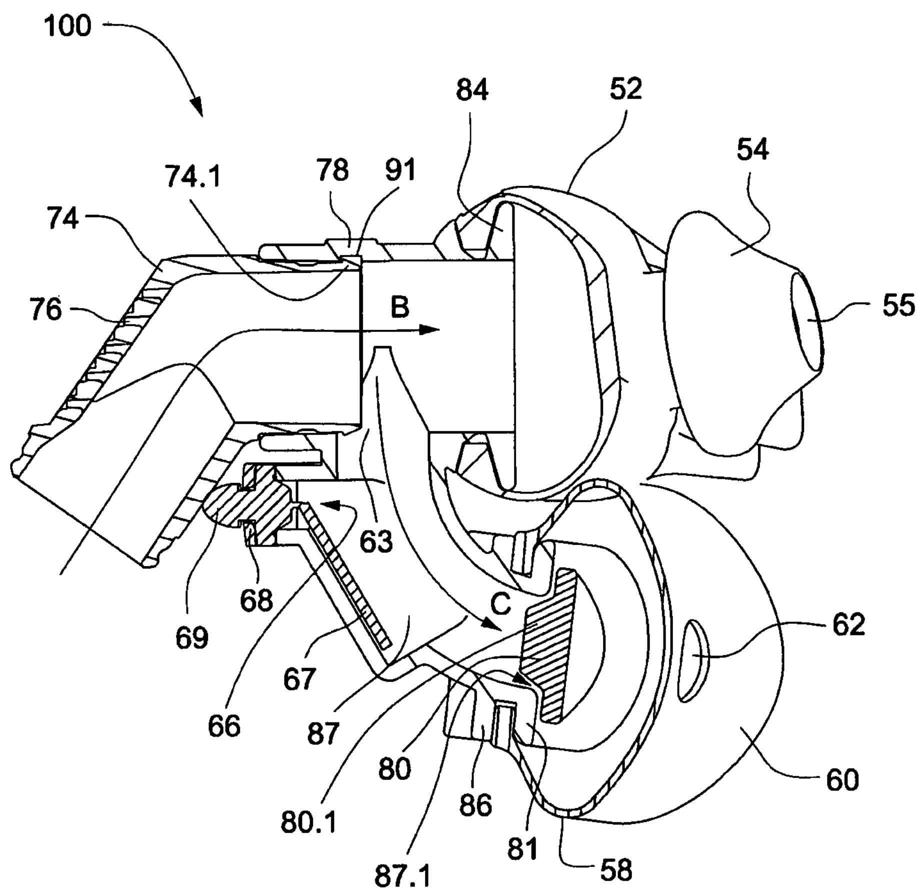
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
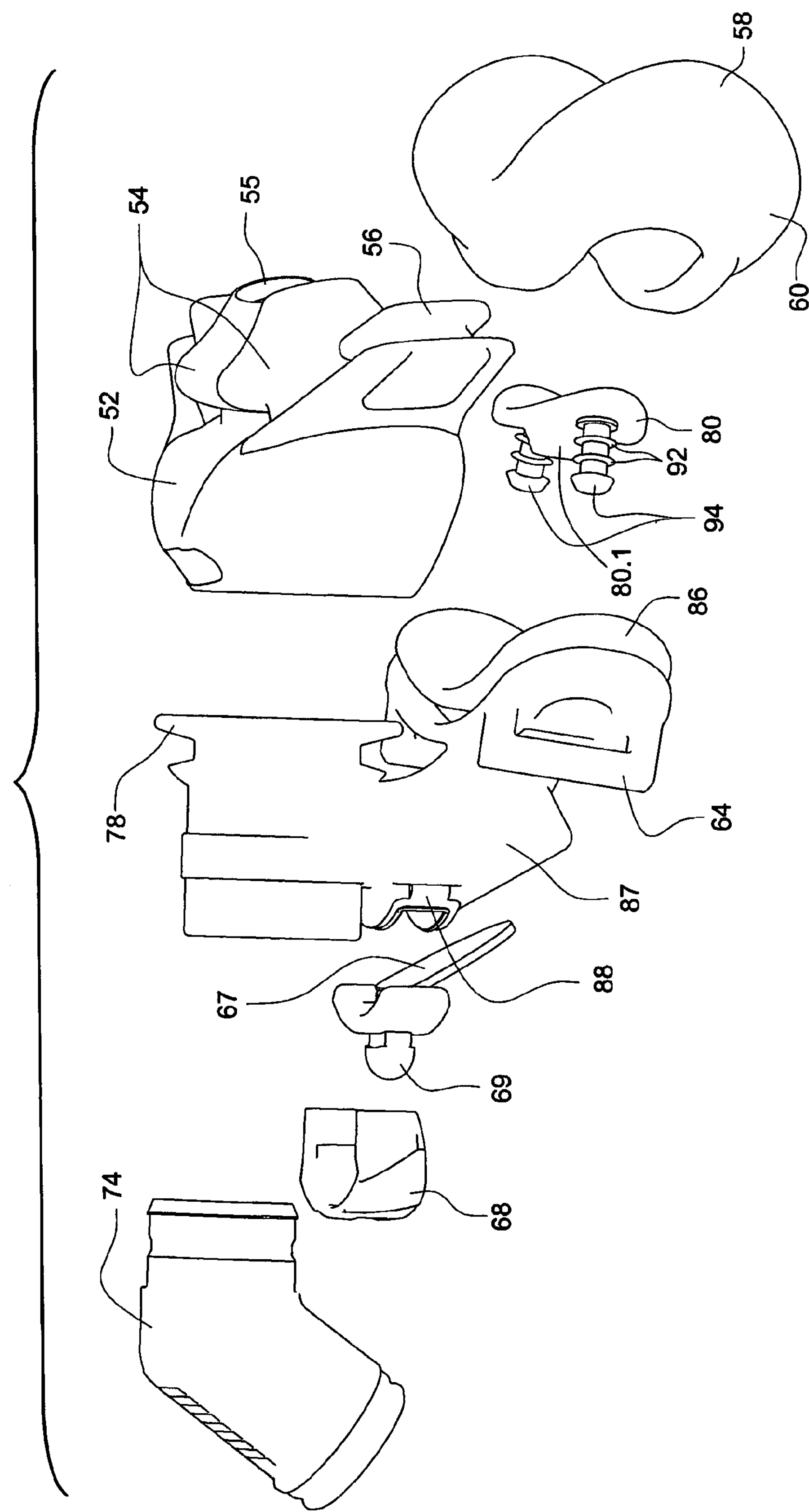
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
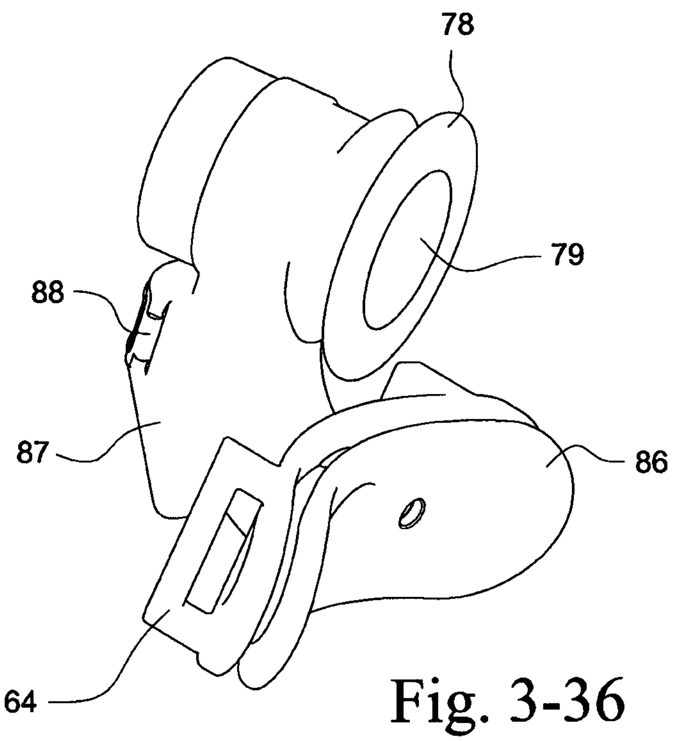
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
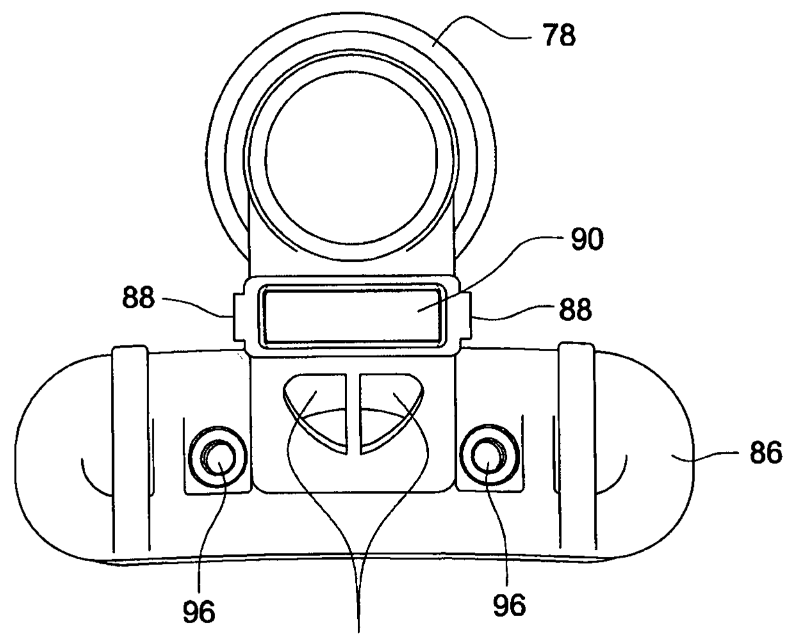
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
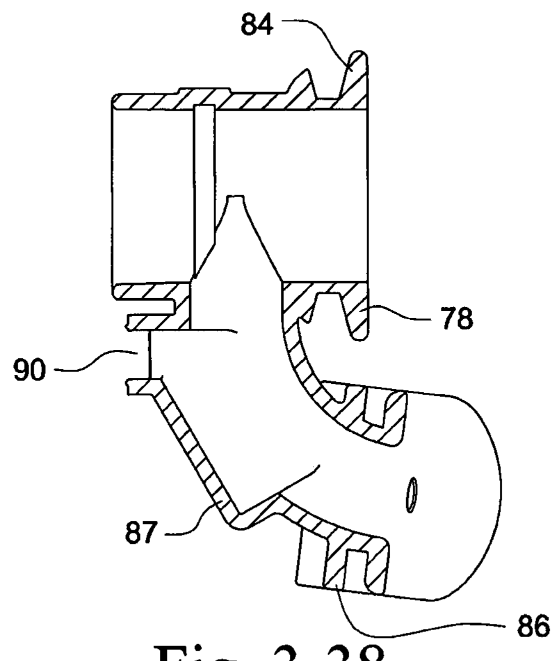
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
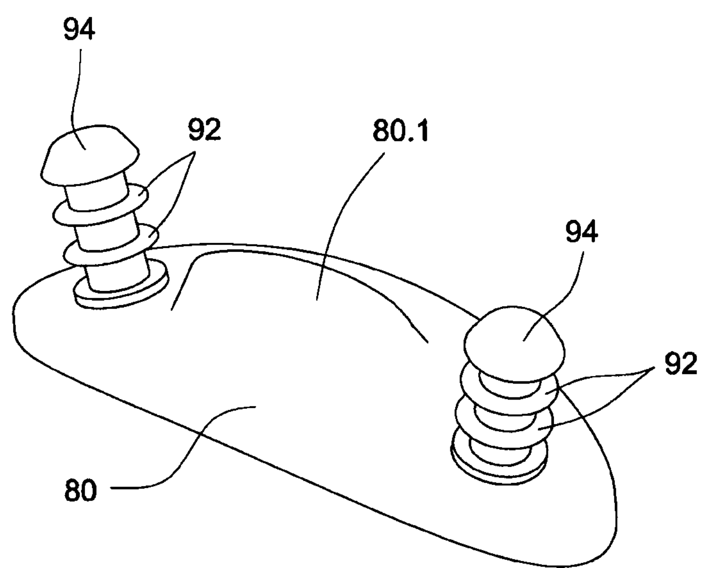
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
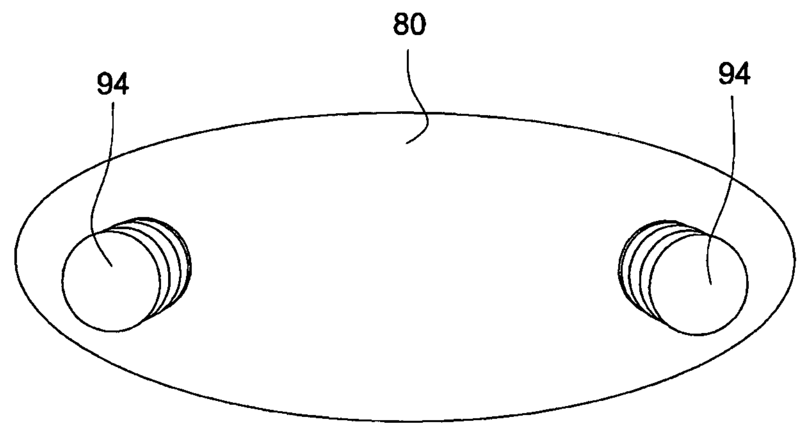
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
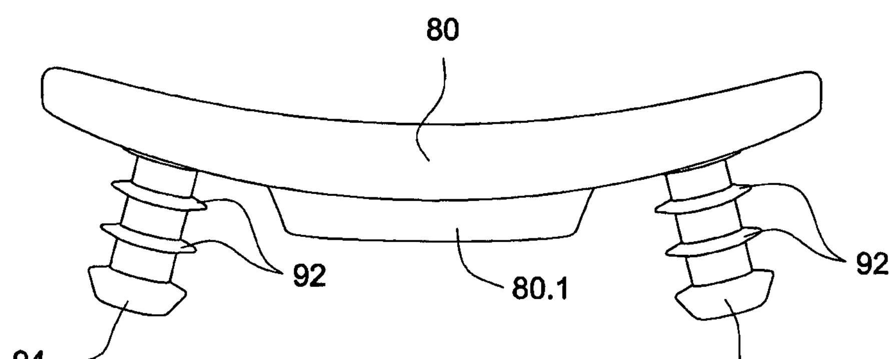
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
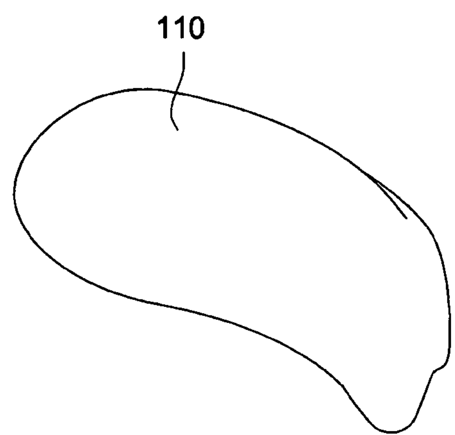
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
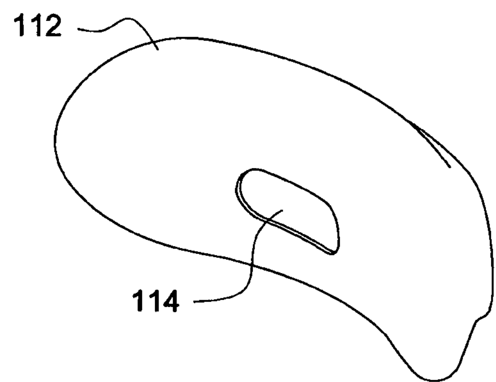
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
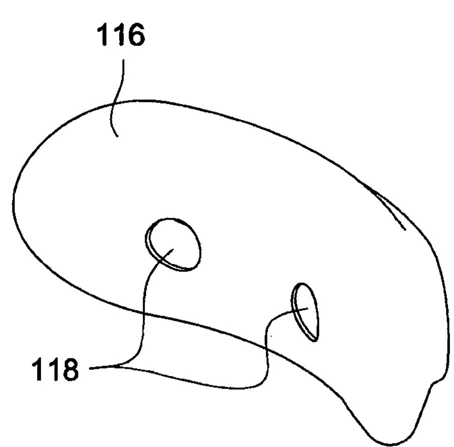
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
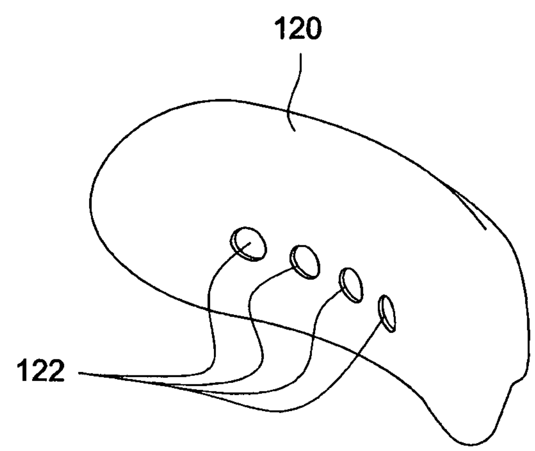
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
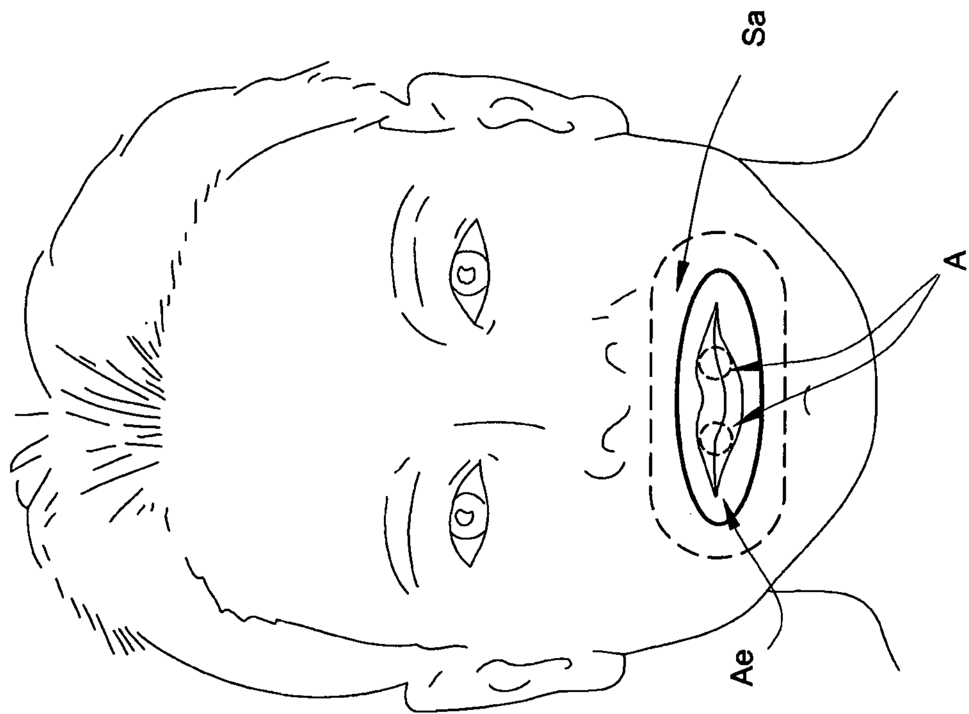
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
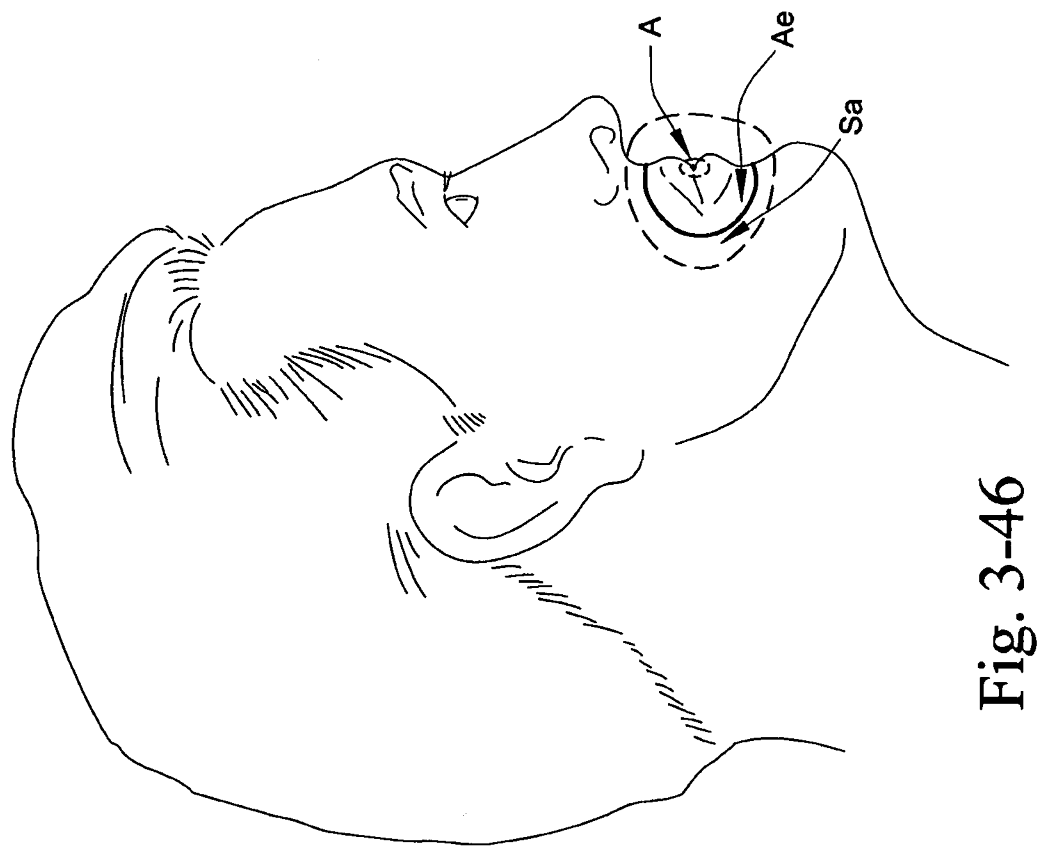

In one form, the present technology comprises a method for treating a respiratory disorder comprising the step of applying positive pressure to the entrance of the airways of a patient 1000 (e.g., see FIG. 1*a*).

5.2.1 Nasal CPAP for OSA

In one form, the present technology comprises a method of treating Obstructive Sleep Apnea in a patient by applying nasal continuous positive airway pressure to the patient.

5.3 Patient Interface

The patient interface or mask system of the present technology delivers pressurized breathable gas to the patient and includes a nasal portion and a mouth portion. The nasal portion may have at least one nasal portion aperture adapted to be in communication with a supply of pressurized gas for delivery to at least one nasal opening of the user. The mouth portion may have at least one mouth portion aperture also adapted to be in communication with the source of the pressurized gas to deliver the pressurized gas to the user's mouth. The at least one mouth portion aperture may be separate from the at least one nasal portion aperture. The patient interface may be adapted to limit a flow of the pressurized gas out of the at least one mouth portion aperture to be no greater than a flow of the pressurized gas out of the at least one nasal portion aperture, or the mouth flow may be set to an absolute maximum, e.g., whichever is less. The patient interface may also be provided with an anti-asphyxia valve (AAV), but it is not necessary to provide an AAV even with an oro-nasal mask, for reasons described herein.

In one form of the present technology, about the same flow rate of air is delivered to both the nasal and oral passages.

In one form of the present technology, about 5% to about 20% of the airflow to the patient is delivered via the mouth, with the remainder being delivered via the nasal passages.

In one form of the present technology, about 20% to about 30% of the airflow to the patient is delivered via the mouth, with the remainder being delivered via the nasal passages.

In one form of the present technology, about 30% to about 40% of the airflow to the patient is delivered via the mouth, with the remainder being delivered via the nasal passages.

In one form of the present technology, about 40% to about 49% of the airflow to the patient is delivered via the mouth, with the remainder being delivered via the nasal passages.

The patient interface provides patients with options for therapy (nares only, nasal with mouth seal, or nares and mouth therapy) without the system becoming too expensive and also improving intuitive use of the patient interface. This allows the patient to use the patient interface without too much or any instruction.

As illustrated in FIGS. 3-1 to 3-11, for example, a patient interface or mask system 1 may include a nasal portion 10 and a mouth portion 20. The patient interface 1 is arranged to form a seal or substantially seal with the nose and mouth of the patient to deliver pressurized gas to the patient. The nasal portion 10 and the mouth portion 20 may be integrally formed, or they may be in the form of separate elements. The patient interface 1 may optionally include a forehead support 40 and headgear (not shown). The forehead support 40 may include one or more forehead cushions 42. An air delivery system may deliver air to the patient interface 1, such as through a flexible tube connected to elbow 30. The elbow 30 may include one or more vents 31 to vent air/$CO_2$ breathed out by the patient. The patient interface 1 limits mouth breathing of the patient by limiting the flow of air or breathable gas to the mouth portion 20, as further described below. While the nasal cushion of the mask system illustrated in FIGS. 3-1 to 3-11 includes a gusset, the gusset is not required.

The nasal portion 10, elbow 30 and forehead support 40 of FIGS. 3-1 to 3-11 may be a known nasal only mask system, such as the ResMed Mirage Activa™ (e.g., as described in U.S. Pat. No. 7,958,893 and U.S. Pat. No. 7,318,439, each of which is incorporated by reference herein in its entirety). The mouth portion 20 and supporting structure may be adapted to be added to and function with the nasal portion 10 of a known nasal only mask system to provide a nasal and mouth patient interface. The resulting nasal and mouth patient interface 1 may limit mouth breathing of the patient by limiting the flow of air or breathable gas to and out of the mouth portion 20.

FIGS. 3-12 to 3-19 illustrate another mask system or patient interface 50, having a nasal portion 52 and a mouth portion 58 adapted to function together to deliver the breathable, pressurized gas to the patient's nares and mouth. The nasal portion 52 and elbow 74 may be a known nasal only mask system, such as the ResMed Swift FX™, (e.g., as described in U.S. Patent Appln. Pub. No. 2010/0307502 A1), which is incorporated by reference herein in its entirety). The mouth portion 58 and supporting structure may be adapted to be added to and function with the nasal portion 52 to provide a nasal and mouth patient interface 50. The nasal and mouth patient interface 50 may limit mouth breathing of the patient by limiting the flow of air or breathable gas out of the mouth portion 58.

The patient interface 50 may limit the flow of air or breathable gas to the mouth portion 58 by utilizing at least one mouth portion aperture 62 having an area selected to limit the flow out of the mouth portion 58 and into the oral cavity of the patient's mouth. Alternatively, the patient interface may limit the flow of air or breathable gas out of the mouth portion 58 by providing structure allowing the user to select one of a plurality of mouth portion flow levels, as further described below.

FIGS. 3-28 to 3-35 illustrate a mask system or patient interface 100, which includes a nasal portion 52 and a mouth portion 58, where the flow of pressurized gas or air out of the mouth portion 58 is also controlled to limit mouth breathing by the user. The patient interface 100 limits the flow of air or breathable gas out of the mouth portion 58 by utilizing either one or more mouth portion apertures 62 or a restrictor, as further described below.

5.3.1 Nasal Portion

The nasal portion is intended to form a seal with the patient's nasal airway in use, and to deliver pressurized breathable gas or air to the patient's nasal airway. The nasal portion could be a seal that is disposed on the outside of the patient's nose, for example, a typical nasal mask. Alternatively, it could be an around the nares type seal like a pillows type mask, or it could be an in the nose type seal like nasal plugs or prongs. A nares seal may be an appropriate choice for patients who have upper airway obstructions. Breathing through the nose may also have other benefits like a natural filtration of the inhaled air.

As illustrated in FIGS. 3-1 to 3-11, the patient interface 1 may include a nasal portion 10. The nasal portion 10 may include a nasal frame portion 12, a nasal chamber 13, a nasal portion cushion 16 (FIG. 3-3), headgear connector receptacles 14 adapted to connect to headgear clips, and a nasal portion aperture 18. The nasal portion cushion 16 and nasal portion aperture 18 are adapted to form a seal on the outside of the patient's nose to deliver the pressurized air or gas to the nasal airways of the patient. As illustrated in FIG. 3-6, pressurized gas or air is delivered through swivel 32 and elbow 30 in the direction of arrow "A" to a chamber of the nasal portion 10, and exhaled gas is exhausted in the direction of arrow B. In another form, the pressurized gas or air is delivered through a swivel elbow.

The frame 12 may include a front aperture or frame aperture 15 (FIG. 3-11) adapted to connect to elbow 30, to deliver the pressurized breathable gas from the elbow 30 to the chamber of the nasal portion 10. Additionally, nasal frame portion 12 may include one or more supplemental gas ports 19 as illustrated in FIG. 3-11. The at least one supplemental gas port 19 may provide a conduit from the chamber of the nasal portion 10 to the outer atmosphere. The supplemental gas ports 19 are typically provided with a cap to allow them to be sealed when not in use, as described in U.S. Pat. No. 7,669,599, incorporated herein by reference in its entirety.

As illustrated in FIGS. 3-12 to 3-19 and FIGS. 3-28 to 3-35, the patient interfaces 50 and 100 include a nasal portion 52. As illustrated in FIGS. 3-18 and 3-34, pressurized gas or air is delivered through elbow 74 along a first passageway or conduit in the direction of arrow "B" to a chamber of the nasal portion 52. The elbow may include one or more vents 76 to vent air/$CO_2$ breathed out by the patient.

The nasal cushion may be moulded, e.g. from liquid silicone rubber (LSR). The nasal cushion may be formed in one piece.

The nasal portion 52 may include at least one nasal cushion 54, each having a nasal portion aperture 55 at its distal end, through which the breathable gas may be delivered to the nasal airways of the patient. The nasal cushions 54 are adapted to form a seal with the nares of the patient. The nasal cushions 54 may be in the form of a pair of nozzles having a generally tapered conical shape to conform with the user's nares. Preferably, the at least one mouth portion aperture 62 has a combined cross sectional area that is equal or smaller than the combined cross sectional area of the nasal air passages of the patient. The smaller cross-sectional area provides a greater resistance to oral breathing and encourages nasal breathing. Thus, the combined cross-sectional area of the one or more oral apertures 62 can be based on statistical data for the dimensions of an average nasal air passage, preferably at its narrowest point. Alternatively, the aperture 62 dimensions can be based on clinical tests on the specific patient, the tests including the patient trying patient interfaces having apertures 62 with different dimensions.

The nasal portion 52 may also include headgear connectors 56 (FIG. 3-19) for connection to headgear. The nasal portion 52 may be adapted for use without the mouth portion 58, by connecting the elbow 74 directly to the nasal portion 52. Alternatively, the nasal portion 52 may be adapted to connect to the adaptor 65 or adaptor 87 to provide a nasal and mouth patient interface.

5.3.2 Mouth Portion

The mouth portion may be adapted to surround and/or confront the patient's mouth and form a seal with the patient's airway at the mouth. The seal of the mouth portion could be a flap type or membrane type seal, or it could be a compression seal utilizing materials such as foam, gel, fabric, etc. The mouth portion may provide a complete seal to prevent any mouth breathing, or limited mouth breathing may be provided by controlling the amount of air or gas flowing to and out of the mouth portion of the patient interface. The mouth portion may have a width of about 50-80 mm and a height of about 20-40 mm.

The seal of the mouth portion may be moulded, e.g. from liquid silicone rubber (LSR).

FIGS. 3-46 and 3-47 show some parameters relevant to the sealing operation of the described patient interface. The total area of the mouth portion apertures 62 is denoted with A. The force to keep the patient interface in place may need to compensate a "blow off" Fb (not shown) that acts upon the patient interface by pushing the patient interface away from the patient's face, when pressurized air is supplied to the patient's airways. The "blow off" force Fb depends on the effective area Ae of the external surface of the patient interface that is exposed to the pressure P within the patient's mouth and its magnitude can be calculated by using the formula $Fb=P\times Ae$. The required inwardly directed compensation force is slightly larger than Fb and is preferably provided by elastic tension, e.g. from a headgear strap. In FIGS. 3-46 and 3-47, the footprint of the area Ae on the patient's face is denoted by a continuous nominally elliptically shaped line surrounding the two apertures 62. A doted elliptical line encircling the area Ae denotes the outer boundary of a sealed area or mouth sealing footprint area Sa across which a section of the mouth portion 58 sealingly overlaps with a section of the patient's face. The continuous elliptically shaped line denotes the inner boundary of this sealed area or mouth sealing footprint area. As the pressure P does not reach beyond the continuous elliptical line and into the sealed area, only a decreasing outward pressure (and hence force) is applied to the patient interface across this area. In an example, the mouth sealing footprint area Sa is about twice an area of the patient's lips. In an example, a width of the mouth sealing footprint area is about equal to a width of the patient's mouth. In an example, the mouth sealing footprint area is substantially equal to a nasal sealing footprint area of the nasal portion.

It is noted that in certain forms of the present technology, the mouth sealing footprint area is significantly smaller than a mouth sealing footprint area of prior art full-face masks. An advantage of such forms of the present technology over such prior full-face masks is a reduction in headgear tension required to secure the patient interface in position.

Here it should be noted that even if the patient interface has no apertures 62 in the mouth section and completely seals the patient's mouth, it still allows breathing out. To achieve that, a patient has to provide a "breathing out" pressure that exceeds the pressure inside the mouth section of the interface. Thus, such a patient interface can act as a one-way valve that allows breathing out, but not breathing in.

A mouth portion 20 as illustrated in FIGS. 3-1 to 3-11 may include mouth portion cushion 22 and a mouth portion frame 26. The mouth portion cushion 22 may include one or more mouth portion apertures 24, through which the pressurized breathable gas may be delivered to the mouth of the patient. As illustrated in FIGS. 3-6 and 3-11, the mouth portion frame 26 may include a conduit 28, through which the air or gas may be delivered to the mouth portion chamber 20.1 and to the mouth portion apertures 24, for delivery to the patient's mouth. The conduit 28 may pass through a portion of support 36, as illustrated in FIG. 3-6. The air may be directed to the conduit 28 by one or more air delivery tubes 37, which may be connected at an opposite end to one or more supplemental gas ports 19. The pressurized gas or air may be directed from nasal chamber 13 of the nasal portion 10 through the supplemental gas port 19, through the air delivery tube and the conduit 28 to the at least one mouth portion aperture 24.

The mouth portion frame 26 may include a support 36. The support 36 may be adapted to secure the mouth portion 20 in place relative to the nasal portion 10, in cooperation with the bracket 43 and nut/dial 39. The support 36 may be substantially rigid or semi-rigid to maintain the relative position between the nasal portion 10 and the mouth portion 20. The support 36 may include a threaded portion 38 adapted to receive a thread of the dial 39, so that the support 36 will move in a direction along an axis of the support 36 when the dial is turned. This selective adjustment mechanism allows a position of the mouth portion 20 to be selectively adjusted by the patient relative to the nasal portion 10 in a direction along an axis of the support 36.

As illustrated in FIG. 3-11, bracket 43 may be adapted to secure the mouth portion 20 to the nasal portion 10. The bracket 43 may include a bracket aperture 44, at least one support aperture 45, a groove or slot 46, a bracket or restrictor sleeve 47, and a clip 48. The bracket aperture 44 may be sized to fit around the frame aperture 15 after removing elbow 30. Replacing elbow 30 then helps secure the bracket 43 in place relative to the nasal portion 10. Bracket 43 may be additionally secured in place by clip 48 secured within a slot 21, which may be on the mouth portion frame 26 or the forehead support 40.

The groove or slot 46 in the bracket 43 may be adapted to receive dial 39, with the threaded portion of support 36 being received by the sleeve 47, the support apertures 45, and the threaded portion of the dial 39 (FIG. 3-6). When the dial 39 is turned, the support 36 will then move in a direction along an axis of the support 36 through the sleeve 47 and support apertures 45, causing the connected mouth portion 20 to move relative to the nasal portion 10.

The mouth portion cushion 22 is further illustrated in FIGS. 3-7 to 3-10. The mouth portion cushion 22 may be shaped to fit a face and mouth region of the patient. For example, the mouth portion cushion 22 may be curved as illustrated in the top view of FIG. 3-9 to fit a curvature of the patient's face/mouth. The mouth portion cushion 22 may have a central portion 33 and an outer border surrounding the central portion and adapted to fit around and/or face the patient's lips.

The mouth portion cushion 22 has an opening 22.1 adapted for connection to the mouth portion frame 26. Connection can be accomplished using a tongue and groove arrangement, e.g., as shown in FIG. 3-6 where the mouth portion cushion 22 forms the tongue and the mouth portion frame 26 forms the groove.

FIGS. 3-12 to 3-19 and 3-28 to 3-35 illustrate a mouth portion 58. The mouth portion 58 may include a mouth cushion 60 and be adapted to connect to an adaptor 65 or 87. The examples of FIGS. 3-12 to 3-19 include adaptor 65, while the examples of FIGS. 3-28 to 3-35 include adaptor 87. The adaptors 65 and 87 are alternative adaptors adapted to connect the mouth portion 58 between the nasal portion 52 and the elbow 74.

The mouth cushion 60 may include one or more mouth portion apertures 62 adapted to deliver the pressurized gas or air to the mouth of the patient. The adaptors 65, 87 may include a mouth cushion engagement portion 86 adapted to secure the mouth cushion 60 in place to the adaptor 65, 87. In particular, the mouth cushion engagement portion 86 includes a U-shaped portion 81 defining a groove adapted to receive an edge or tongue of the mouth cushion 60, to secure the mouth cushion to the adaptor 65, 87, as illustrated in FIGS. 3-18 and 3-34.

FIGS. 3-42 to 3-45 illustrate alternative removably replaceable mouth portion cushions 110, 112, 116 and 120 that may be utilized with the patient interfaces 1, 50 or 100. Mouth portion cushion 110 includes no mouth portion apertures and hence will act as a mouth seal when utilized with the patient interfaces 1, 50 or 100, in which case gas will be delivered only to the patient's nasal passages. Mouth portion cushion 112 has a single mouth portion aperture 114. Mouth portion cushion 116 has two mouth portion apertures 118. Mouth portion cushion 120 has four mouth portion apertures 122. Any number of mouth portion apertures may be utilized. A total area of the mouth portion apertures may be utilized to control a flow of the pressurized air or gas to the mouth to limit mouth breathing. The utilization of the area of the mouth portion apertures to limit flow to the mouth may be utilized or combined with other structure to limit mouth breathing, such as utilizing the restrictor portion 80 (FIG. 3-23).

5.3.3 Adaptor

The adaptors 65 and 87 share some common parts which have like reference numerals. The adaptors 65 and 87 are both adapted to connect the mouth portion 58 to the nasal portion 10 or 52 and to the elbow 74. The adaptors 65, 87 deliver the pressurized breathable gas or air through adaptor aperture 63 along a second passageway or conduit in the direction of arrow "C" to the mouth portion 58. In addition, the adaptor 65 may optionally be adapted to provide a patient selectable level of air or gas flow out of the mouth portion 58, to control mouth breathing of the patient. Both patient user interfaces 50 and 100 may utilize other means to control the flow of air or gas out of the mouth portion 58 to be no more than the flow of air or gas to the nasal portion 10, or to a lower fixed or absolute level, to control mouth breathing of the patient.

The adaptors 65, 87 may include headgear connectors 64 adapted to connect to headgear, and may optionally include an anti-asphyxia valve 66 (AAV). As illustrated in FIGS. 3-18 and 3-34, the adaptor 65, 87 may provide a first air passageway or conduit along arrow "B" from elbow 74 to mouth portion 58, and a second air passageway or conduit along arrow "C" through adaptor 65, 87 to the mouth portion 58. The pressurized air or gas may be directed from the elbow 74 to split and follow the conduits along the directions of arrows "B" and "C", so that a portion of the pressurized air or gas is directed to the nasal portion 52 and a portion of the pressurized air or gas is directed to the mouth portion 58.

The AAV 66 is adapted to allow the patient to breath to the atmosphere in the event that the pressurized gas or air stops flowing through the patient interface. The AAV 66 may include AAV flap 67, AAV clip 68 and AAV tab 69. The AAV 66 is adapted to be attached to the adaptors 65, 87. As illustrated in FIGS. 3-21 and 3-37, the adaptors 65, 87 may include at least one AAV aperture or conduit 57, AAV aperture 90 and protrusions 88. The AAV flap 67 is adapted to fit into AAV aperture 90 and cover AAV conduits 57 when the AAV 66 is inserted, and the flow of the pressurized gas or air through the adaptor 65, 87 urges the AAV flap 67 into the closed position. The AAV flap 67 may be biased to open in the absence of the pressurized gas or air, allowing the patient to breathe through the mouth portion 58 and the AAV conduits 57 to the atmosphere.

The AAV 66 may be secured to the adaptor 65, 87 by the AAV clip 68. The AAV clip 68 may have an engagement aperture 71 (FIG. 3-19) adapted to receive the AAV tab 69, with the edge portions 75 of the AAV clip 68 adapted to fit over and secure to the protrusions 88 on the adaptor 65, 87. The AAV tab 69 may function as a quick disconnect for the AAV 66, where a user pulling on the AAV tab 69 may cause disconnection of the AAV clip 68 from the adaptor 65, 87, allowing the AAV flap 67 and clip to be removed together as a unit.

The patient interface 50 is adapted to provide a user selectable level of pressurized air or gas flow to the mouth portion 58, to control mouth breathing of the patient. The adaptor 65 may include flow control indicators 72, which may include, for example, numbered indicators used to indicate selectable levels of flow to the patient or user. The flow control indicators 72 are adapted to function with restrictor portion 80, to allow the user to select from among a plurality of mouth portion flow levels. The restrictor portion 80 is adapted to step-wisely adjust the flow of the pressurized gas that is delivered to the mouth portion and through the at least one mouth portion aperture 62. The restrictor portion 80 can be adjusted between a completely closed configuration, where any mouth breathing is prevented, to a completely open configuration, in which free mouth breathing is allowed.

As illustrated in FIG. 3-23, the restrictor portion 80 is hollow and includes a dial 70 and a restrictor portion aperture 82. To allow connection to the adaptor, restrictor portion 80 may include a plurality of arms each terminating in a ridge portion 85 and separated by slots 83. Arms may resiliently deform upon insertion, and snap into place such that the ridge portions are held in place, as shown in FIG. 3-18. The dial 70 may include a flow position indicator 73, as illustrated in FIGS. 3-13 and 3-24, which may turn with dial 70 to indicate one of the selectable levels of flow by pointing to one of the flow control indicators 72.

The restrictor portion 80 is adapted to fit within the adaptor 65, with the restrictor portion aperture 82 being selectively alignable with the adaptor aperture 63, as illustrated in FIG. 3-18. Turning of the dial 70 to one of the selectable flow positions, being user selectable positions, causes turning of the entire restrictor portion 80, so that at each position, a different proportion of the restrictor portion aperture 82 communicates with the adaptor aperture 63, resulting in a different flow level. The restrictor portion 80 is illustrated in FIG. 3-26 in a first flow position and is illustrated in FIG. 3-27 in a second flow position. The flow position of the restrictor portion 80 in FIG. 3-26 may be a more open flow position (more overlap with aperture 63) allowing a higher level of flow than illustrated in FIG. 3-27.

The adaptor 65 includes a nasal portion interface 78 adapted to engage with the nasal portion 52 (FIG. 3-19). The nasal portion interface 78 includes a nasal portion interface aperture 79 and a nasal portion engagement portion 84 adapted to engage with the nasal portion 52. The nasal portion engagement portion 84 may be U-shaped or include a groove as illustrated in FIG. 3-18, for example, to receive and secure an edge or tongue of the nasal portion 52. The nasal portion engagement portion 84 may be a first fitting adapted to connect to an aperture of the nasal portion 52. The restrictor portion 80 may also be adapted to connect to, e.g., receive, the elbow 74, and may include an interior recess 91 to receive an engagement portion or ridge 74.1 of the elbow 74, as illustrated in FIGS. 3-18 and 3-34.

The restrictor portion 80 is inserted into the adaptor 65 until the ridge portion 85 engages with an edge of the nasal portion engagement portion 84, as illustrated in FIG. 3-18. The flexibility of the end of the restrictor portion 80 provided by the slots 83 allows the end of the restrictor portion 80 to flex inwards while being inserted into nasal portion engagement portion 84, and then flex outwards so that the ridge portion 85 engages with the edge of the nasal portion engagement portion 84 to secure the restrictor portion 80 in place.

In either of the adaptors 65 or 87, an area or size of the adaptor aperture 63 may be selected to limit a flow of the pressurized air or gas to and out of the mouth portion 58 to control mouth breathing of the patient. The area may be selected to limit the flow of the pressurized air or gas to the mouth portion to be no greater than the flow to the nasal portion 52, or to a different or lower flow, e.g., a fixed or absolute value. The flow to the mouth portion 58 may be further selectively controlled by the restrictor portion 80 in patient interface 50.

The restrictor portion 80 is shown in FIGS. 3-34, 3-35 and 3-39 to 3-41. The restrictor portion 80 includes at least one protrusion 94, or one or more protrusions 94 (shown in FIGS. 3-35 and 3-39, but not shown in FIG. 3-34), each adapted to fit within a corresponding mouth frame aperture 96 (see FIG. 3-37). In one form of the present technology the patient interface includes at least one mouth frame aperture 96. The protrusions 94 are adapted to engage with corresponding mouth frame apertures 96 in a variable manner, by engaging one or more of a plurality of resilient rings 92 to a predetermined depth within the corresponding mouth frame aperture 96. By controlling the insertion depth of protrusions 94 within the corresponding mouth frame apertures 96, one effectively controls the insertion of a protrusion 80.1 (see FIGS. 3-34 and 3-39) into a mouth outlet 87.1 (see FIG. 3-34), thereby controlling the flow delivered to the mouth portion chamber and apertures 62.

5.3.4 Modular Patient Interface

The patient interface examples disclosed herein may include a nasal portion and a mouth portion that deliver the pressurized air or gas to the patient's nose and mouth. The patient interface systems may be adapted to allow a patient to selectively utilize the nasal portion alone in a nasal only mode to deliver the pressurized air or gas to the patient's nose only, or to use the nasal portion and mouth portion together in a nasal and mouth mode to deliver the pressurized air or gas to the patient's nose and mouth. In the nasal and mouth mode, the patient interface may be adapted to limit the flow of the pressurized gas to the mouth portion to be no more than the flow of the pressurized gas to the nasal portion to limit mouth breathing of the patient, or to a different or lower flow.

To utilize the patient interface in the nasal only mode, the mouth portion may be removed from the patient interface. In the examples of FIGS. 3-1 to 3-11, the mouth portion 20 is removed by disconnecting air delivery tube 37 and elbow 30, and removing bracket 43 along with the attached mouth portion 20, mouth portion frame 26 and dial 39. The elbow 30 is then reconnected to the frame 12 and the patient interface may be used in the nasal only mode. The supplemental gas port 19 may be capped to prevent escape of the pressurized gas from the nasal portion 10.

In the examples of FIGS. 3-12 to 3-19 and 3-28 to 3-35, the mouth portion 58 is removed by disconnecting elbow 74, and removing adaptor 65, 87 along with the attached mouth portion 58, and connecting the elbow to the nasal portion 52. The elbow 74 may then be connected to the nasal portion 52.

5.3.5 Retrofit Kits

Retrofit kits may be provided to convert an existing nasal (nares) only mask or patient interface that delivers pressurized air or gas only to the patient's nose into a nasal and mouth patient interface that delivers the pressurized air or gas to the patient's nose and mouth. The retrofit kits may include a mouth portion for forming a seal with and delivering pressurized gas to a patient's mouth, and structure for connecting the mouth portion to the nasal only patient interface. The retrofit kit may be adapted to limit the flow of pressurized air or gas to the mouth portion to be no more than the flow of pressurized air or gas delivered to the nasal portion, or to limit the flow of pressurized air or gas to the mouth portion to a lower level, to limit mouth breathing of the patient. Further, the retrofit kit may be adapted to allow the user to select among one of a plurality of flow levels of the pressurized gas to be delivered to the mouth portion. The flow levels may all be adapted to limit mouth breathing of the patient.

In the examples of FIGS. 3-1 to 3-11, the existing mask may include nasal portion 10 with forehead support 40 and elbow 30 along with headgear (not shown). The retrofit kit may include the mouth portion 20 including the mouth portion frame 26, the air delivery tube 37, and flow limitation structure adapted to limit the flow of the pressurized gas out of the mouth portion to be no more than the flow of the pressurized gas provided out of the nasal portion. The flow limitation structure may include the mouth cushions 60 having at least one aperture 62 having an area to limit the flow of the pressurized gas out of the mouth portion 58.

In the examples of FIGS. 3-12 to 3-19, the existing mask may include nasal portion 52 and elbow 74 along with headgear (not shown). The retrofit kit may include the mouth portion 58, the adaptor 65, and structure adapted to limit a flow of the pressurized gas out of the mouth portion 58 to be no more than the flow of the pressurized gas provided out of the nasal portion 52 to the nares of the user. The structure adapted to limit a flow of the pressurized gas out of the mouth portion 58 may include the restrictor portion 80 and/or the mouth cushions 60 having at least one aperture 62 having an area to limit the flow of the pressurized gas out of the mouth portion 58. The retrofit kits may optionally include the AAV 66.

The patient interface systems described herein may be used to provide respiratory therapy to a patient's nares only, or to both a patient's nares and mouth. For example, the respiratory therapy may be initially provided to the patient's nares only, and then periodically changed from being applied to the patient's nares only to being applied to the patient's nares and mouth.

5.3.6 Method of Operation

Another aspect of the present technology is a method of operating a device for treating a respiratory disorder.

In one form, the method comprises the following steps:

(i) Provide a patient with a nasal-only mask and initiate treatment;

(ii) Perform a first monitoring of the patient for an indication of flow limitation or upper airway obstruction, e.g., an Apnea-Hypopnea Index (AHI), or treatment pressure in an automatically adjusting CPAP device, while the patient is wearing the nasal-only mask;

(iii) Provide the patient with a patient interface apparatus in accordance with the present technology and initiate treatment;

(iv) Perform a second monitoring of the patient for an indication of flow limitation or upper airway obstruction, e.g., an Apnea-Hypopnea Index (AHI), or treatment pressure in an automatically adjusting CPAP device, while the patient is wearing the patient interface in accordance with the present technology; and (v) Compare the first and second monitoring steps and determine whether the outcome of the second monitoring step indicates that the patient has a higher or higher treatment pressure than the first monitoring step; and if it does then reduce the relative oral flow.

In another form, the method comprises the following steps:

(i) Provide a patient with a full-face mask and initiate treatment;

(ii) Perform a first monitoring of the patient for an indication of flow limitation or upper airway obstruction, e.g. an Apnea-Hypopnea Index (AHD, or treatment pressure in an automatically adjusting CPAP device, while the patient is wearing the full-face mask;

(iii) Provide the patient with a patient interface apparatus in accordance with the present technology and initiate treatment;

(iv) Perform a second monitoring of the patient for an indication of flow limitation or upper airway obstruction, e.g. an Apnea-Hypopnea Index (AHI), or treatment pressure in an automatically adjusting CPAP device, while the patient is wearing the patient interface in accordance with the present technology; and (v) Compare the first and second monitoring steps and determine whether the outcome of the second monitoring step indicates that the patient has about the same AHI, or same treatment pressure than the first monitoring step; and if it does then reduce the relative oral flow.

5.3.7 Other Remarks

An advantage of certain forms of the present technology is that it addresses the problem of mouth breathing, or mouth leaks that patients can experience when wearing nasal-only masks.

An advantage of certain forms of the present technology is that it may be more comfortable for patients who feel claustrophobic while wearing a full-face mask.

An advantage of certain forms of the present technology is that it may be more comfortable for patients who feel claustrophobic while wearing a device which allows no oral flow, or attempts to eliminate mouth flow, such as a chin strap, or mouth seal.

An advantage of certain forms of the present technology is that it may be more comfortable for patients who feel claustrophobic while wearing a device which provides very little oral flow, e.g., about 5% or less.

Another advantage of certain forms of the present technology, for example compared with, e.g., a chin strap, or a mouth seal, is that it readily permits patients to open their mouths, e.g., to speak or to yawn or cough.

Another advantage of certain forms of the present technology is that they are at least one of much simpler, comfortable and easier to use ways of overcoming mouth breathing or mouth leaks than other apparatus, such as chin-straps, and tape.

An advantage of certain forms of the present technology when compared to certain oro-nasal or full-face masks, is that certain forms of the present technology avoid placing excessive force on the mandible in a rearward or anterior to posterior direction.

An advantage of certain forms of the present technology is that they place relatively little pressure on the lower or inferior lip of the patient.

An advantage of certain forms of the present technology is that they may be effective with a reduced level of headgear tension than prior art patient interfaces, e.g. prior full face masks, and have an increased level of comfort and patient compliance.

5.4 PAP Device 4000

A PAP device 4000 in accordance with one aspect of the present technology comprises mechanical and pneumatic components, electrical components and is programmed to execute one or more algorithms. In an example, PAP device has an external housing, e.g., formed in two parts, an upper portion 4012 of the external housing, and a lower portion 4014 of the external housing. In alternative forms, the external housing may include one or more panel(s) 4015. In an example, the PAP device 4000 comprises a chassis 4016 that supports one or more internal components of the PAP device 4000. In one form a pneumatic block is supported by, or formed as part of the chassis 4016. The PAP device 4000 may include a handle 4018.

In an example, pneumatic path of the PAP device 4000 comprises an inlet air filter 4112, an inlet muffler, a controllable source of air at positive pressure (e.g., a blower 4142), and an outlet muffler. One or more pressure sensors and flow sensors are included in the pneumatic path.

In an example, pneumatic block comprises a portion of the pneumatic path that is located within the external housing.

In an example, the PAP device 4000 has an electrical power supply 4210, one or more input devices 4220, a processor, a pressure device controller, one or more protection circuits, memory, transducers, data communication interface and one or more output devices. Electrical components may be mounted on a single Printed Circuit Board Assembly (PCBA) 4202. In an alternative form, the PAP device 4000 may include more than one PCBA 4202.

The processor of the PAP device 4000 is programmed to execute a series of algorithm modules in use, e.g., including pre-processing transducer signals module, a therapy engine module, a pressure control module, and further e.g., a fault condition module.

5.5 Glossary

In certain forms of the present technology, one or more of the following definitions may apply. In other forms of the present technology, alternative definitions may apply.

5.5.1 General

Air: Air will be taken to include breathable gases, for example air with supplemental oxygen.

Positive Airway Pressure (PAP): PAP treatment will be taken to mean the application of a supply of air or breathable gas to the entrance to the airways at a pressure that is positive with respect to atmosphere. In one form, the pressure will be continuously positive (CPAP) and e.g., approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms the pressure will be a number of centimeters, e.g. about 5-15 cm of water pressure higher during inhalation than exhalation, and provide ventilatory support. In some forms, the pressure will vary between different respiratory cycles of the patient, for example being increased in response to detection of indications of partial upper airway obstruction, and decreased in the absence of indications of partial upper airway obstruction.

5.5.2 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises e.g. the nasal bones, the frontal process of the maxillae and the nasal part of the frontal bone.

(nose) Cartilaginous framework: The cartilaginous framework of the nose comprises, e.g., the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.5.3 Anatomy of the skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

5.5.6 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow or air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: In certain forms of the present technology, frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. In an example, the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane, e.g., in the context of a sealing portion and/or face-contacting portion, will be taken to mean a typically thin element that has, e.g., substantially no resistance to bending, but has resistance to being stretched.

Seal: The noun form ("a seal") will be taken to mean a structure or barrier that intentionally resists the flow of air through the interface of two surfaces. The verb form ("to seal") will be taken to mean to resist a flow of air.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, e.g., independently, e.g., under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components, e.g., comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.5.7 Terms Used in Relation to Patient Interface

Resilient: Able to deform substantially elastically, and to release substantially all of the energy upon unloading, e.g. within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.6 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used or as being an example to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

6 REFERENCE SIGNS LIST patient interface 1
nasal portion 10
nasal frame portion 12
nasal chamber 13
headgear connector receptacle 14 frame aperture 15
nasal portion cushion 16
nasal portion aperture 18
supplemental gas port 19
mouth portion 20
mouth portion chamber 20.1
slot 21
mouth portion cushion 22
opening 22.1
mouth portion aperture 24
mouth portion frame 26
conduit 28
elbow 30
vent 31
swivel 32
central portion 33
support 36
air delivery tube 37
threaded portion 38
nut/dial 39
forehead support 40
forehead cushion 42
bracket 43
bracket aperture 44
support aperture 45
groove or slot 46
restrictor sleeve 47
clip 48
patient interface 50
nasal portion 52
nasal cushion 54
nasal portion aperture 55
headgear connector 56
mouth portion 58
mouth cushion 60
aperture 62
adaptor aperture 63
headgear connector 64
adaptor 65
anti-asphyxia valve 66
aav flap 67
aav clip, 68
aav tab 69
dial 70
engagement aperture 71
flow control indicator 72
flow position indicator 73
elbow 74
ridge 74.1
edge portion 75
vent 76
nasal portion interface 78
nasal portion interface aperture 79
restrictor portion 80
protrusion 80.1
portion 81
restrictor portion aperture 82
slot 83
nasal portion engagement portion 84
ridge portion 85
mouth cushion engagement portion 86
adaptor 87
mouth outlet 87.1
protrusion 88
aav aperture 90
interior recess 91
resilient ring 92
protrusion 94
mouth frame aperture 96
patient interface 100
replaceable mouth portion cushion 110
replaceable mouth portion cushion 112
single mouth portion aperture 114
replaceable mouth portion cushion 116
mouth portion aperture 118
replaceable mouth portion cushion 120
mouth portion aperture 122
patient 1000
bed partner 1100
patient interface 3000
pap device 4000
upper portion 4012
lower portion 4014
panels 4015
chassis 4016
handle 4018
inlet air filter 4112
blower 4142
air circuit 4170
PCBA 4202
electrical power supply 4210
input devices 4220
humidifier 5000

What is claimed is:

1. A patient interface for treatment of a user having a respiratory disorder, the patient interface comprising:

a nasal portion including a nasal chamber adapted to be in communication with a supply of pressurized gas and at least one nasal portion aperture to permit delivery of the pressurized gas into at least one nasal opening of the user;

a mouth portion including a mouth chamber adapted to be in communication with the supply of pressurized gas and at least one mouth portion aperture to permit delivery of the pressurized gas into an oral cavity of the user's mouth, wherein the nasal chamber of the nasal portion is in direct communication with the mouth chamber of the mouth portion, and wherein the at least one mouth portion aperture is separate from the at least one nasal portion aperture; and a user selectable restrictor portion adapted to be selectively positioned by the user in a plurality of user selectable positions, the user selectable restrictor portion including only a single valve structured and arranged to allocate a flow of the pressurized gas to the nasal chamber and the mouth chamber so as to limit a flow of the pressurized gas from said supply of pressurized gas out of the at least one mouth portion aperture and into said oral cavity of the user's mouth to be up to but no greater than a flow of the pressurized gas from said supply of pressurized gas out of the at least one nasal portion aperture and into said at least one nasal opening for each of the plurality of user selectable positions, the user selectable restrictor portion including at least one of (i) a first flow position in which the flow of the pressurized gas out of the at least one mouth portion aperture is the same as the flow of the pressurized gas out of the at least one nasal portion aperture, and (ii) a plurality of second flow positions in which the flow of the pressurized as out of the at least one mouth portion aperture is less than the flow of the pressurized gas out of the at least one nasal portion aperture.

2. The patient interface of claim 1, wherein the at least one mouth portion aperture has an area no greater than an area of the at least one nasal portion aperture.

3. The patient interface of claim 1, wherein the at least one mouth portion aperture has an area less than an area of the at least one nasal portion aperture.

4. The patient interface of claim 1, wherein the at least one mouth portion aperture comprises a plurality of mouth portion apertures.

5. The patient interface of claim 1, further comprising an air delivery tube configured to deliver the pressurized gas to the mouth portion.

6. The patient interface of claim 5, wherein the nasal portion includes a frame portion having at least one supplemental gas port.

7. The patient interface of claim 6, wherein the air delivery tube is connected to the at least one supplemental gas port to deliver the pressurized gas to the mouth portion.

8. The patient interface of claim 1, further comprising structure adapted to connect the nasal portion to the mouth portion.

9. The patient interface of claim 8, wherein the structure adapted to connect the nasal portion to the mouth portion includes a support having a threaded portion and a dial adapted to engage the threaded portion, the dial and the threaded portion being adapted to adjust a position of the mouth portion relative to the nasal portion by turning of the dial.

10. The patient interface of claim 9, wherein the structure adapted to connect the nasal portion to the mouth portion further includes a bracket having at least one support aperture adapted to engage the support and a groove adapted to engage the dial.

11. The patient interface of claim 10, wherein the bracket further includes a bracket aperture adapted to engage with the nasal portion.

12. The patient interface of claim 11, wherein the nasal portion includes a frame portion having a front aperture adapted to receive an elbow, the elbow adapted to deliver the pressurized gas to the nasal portion, wherein the bracket aperture is adapted to be received by the frame around the front aperture of the frame.

13. The patient interface of claim 12, wherein the support is mounted on a mouth portion frame, the at least one mouth portion aperture being formed in a mouth portion cushion, the mouth portion frame adapted to engage with the mouth portion cushion.

14. The patient interface of claim 13, wherein the mouth portion fame further includes a conduit adapted to receive an air delivery tube to deliver the pressurized gas to the at least one mouth portion aperture.

15. The patient interface of claim 9, wherein the support is substantially rigid or semi-rigid to maintain a relative position between the nasal portion and the mouth portion.

16. The patient interface of claim 9, wherein the mouth portion further comprises a plurality of removably replaceable mouth cushions, each of the mouth cushions having the at least one mouth portion aperture, an area of the at least one mouth portion aperture being different for each of the mouth cushions such that each mouth cushion provides a different flow of the pressurized gas to the mouth of the patient.

17. The patient interface of claim 1, wherein the nasal portion includes a nasal sealing portion adapted to form a seal with at least one nasal opening of the user and the nasal sealing portion has the at least one nasal portion aperture, wherein the mouth portion includes a mouth sealing portion adapted to form a seal with an oral cavity of the user's mouth and the mouth sealing portion has the at least one mouth portion aperture, and wherein the at least one mouth portion aperture has a cross-sectional area no greater than a cross-sectional area of the at least one nasal portion aperture.

18. The patient interface of claim 1, wherein the user selectable restrictor portion is adapted to adjustably limit the flow of the pressurized gas out of the at least one mouth portion aperture and into said oral cavity of the user's mouth to a set upper limit between zero flow and up to the same flow as the flow of the pressurized gas out of the at least one nasal portion aperture and into said at least one nasal opening.

19. The patient interface of claim 1, wherein the single valve is positioned in a fluid communication passageway between the nasal chamber of the nasal portion and the mouth chamber of the mouth portion.

20. A patient interface for treatment of a user having a respiratory disorder, the patient interface comprising:

a nasal portion adapted to be in communication with a source of pressurized gas for delivery to at least one nasal opening of the user;

a mouth portion also adapted to be in communication with the source of the pressurized gas, said mouth portion having at least one aperture to deliver the pressurized gas to an oral cavity of the user's mouth; and an adaptor to couple the mouth portion to the nasal portion, the adaptor including a first conduit portion to convey said pressurized gas to a nasal chamber of the nasal portion, and a second conduit portion to convey pressurized gas to a mouth chamber of the mouth portion, the second conduit portion depending from the first conduit portion such that the nasal chamber is in direct communication with the mouth chamber, wherein the adaptor includes a user selectable restrictor portion adapted to be selective positioned by the user in a plurality of user selectable positions, the user selectable restrictor portion including only a single valve structured and arranged to control a flow of the pressurized gas provided to the nasal chamber and the mouth chamber so as to limit a flow of the pressurized gas out of the at least one aperture of the mouth portion to be up to but no greater than a flow of the pressurized gas to the nasal portion for each of the plurality of user selectable positions.

21. The patient interface of claim 20, wherein the first conduit includes a first fitting to connect to an aperture of the nasal portion, and a second fitting to be coupled with a swivel elbow that is also matingly engageable with the aperture of the nasal portion.

22. The patient interface of claim 20, wherein the structure adapted to limit a flow of the pressurized gas out of the at least one aperture of the mouth portion farther comprises a plurality of removably replaceable mouth cushions, each of the mouth cushions having at least one mouth portion aperture, an area of the at least one mouth portion aperture being different for each of the mouth cushions such that each mouth cushion provides a different flow of the pressurized gas to the mouth of the patient.

23. The patient interface of claim 20, wherein the single valve is positioned in a fluid communication passageway between the nasal chamber of the nasal portion and the mouth chamber of the mouth portion.

24. The patient interface of claim 20, wherein the user selectable restrictor portion includes at least one of (i) a first flow position in which the flow of the pressurized gas out of the at least one aperture of the mouth portion is the same as the flow of the pressurized gas to the nasal portion, and (ii) a plurality of second flow positions in which the flow of the pressurized gas out of the at least aperture of the mouth portion is less than the flow of the pressurized gas to the nasal portion.

25. A retrofit kit for converting a nasal-only mask for treatment of a user having a respiratory disorder to a mouth and nasal mask, the nasal only mask having a nasal portion adapted to provide a flow of pressurized gas to nares of the user and having an aperture adapted to receive an elbow, the retrofit kit comprising:

a mouth portion including a mouth chamber;

an adaptor including a first conduit, the first conduit having a first end to connect with the aperture of the nasal portion and a second end adapted to receive the elbow, the adaptor further including a second conduit extending from the first conduit and in pressure communication with the first conduit and the mouth chamber of the mouth portion; and a user selectable restrictor portion adapted to be selectively positioned by the user in a plurality of user selectable positions, the user selectable restrictor portion including only a single valve structured and arranged to control a flow of the pressurized gas provided to the nasal portion and the mouth portion so as to limit a flow of the pressurized gas out of the mouth portion to be up to but no more than the flow of the pressurized gas provided out of the nasal portion to the nares of the user for each of the plurality of user selectable positions, the user selectable restrictor portion including at least one of (i) a first flow position in which the flow of the pressurized gas out of the mouth portion is the same as the flow of the pressurized out of the nasal portion, and (ii) a plurality of second flow positions in which the flow of the pressurized gas out of the mouth portion is less than the flow of the pressurized gas out of the nasal portion.

26. The retrofit kit of claim 25, wherein the restrictor portion is adapted to step-wisely adjust the flow of the pressurized gas out of the mouth portion.

27. The retrofit kit of claim 25, wherein the structure adapted to limit a flow of the pressurized gas out of the mouth portion further comprises a plurality of removably replaceable mouth cushions, each of the mouth cushions having at least one mouth portion aperture, an area of the at least one mouth portion aperture being different for each of the mouth cushions such that each mouth cushion provides a different flow of the pressurized gas to the mouth of a patient.

28. A retrofit kit for converting a nasal-only mask for treatment of a user having a respiratory disorder to a mouth and nasal mask, the nasal only mask having a nasal portion with a nasal chamber adapted to provide a flow of pressurized gas to nares of the user, and having an aperture adapted to receive an elbow, the retrofit kit comprising:

a mouth portion;

structure adapted to connect the nasal portion to the mouth portion;

an air delivery tube to connect the nasal chamber of the nasal portion to the mouth portion; and a flow limitation structure including a user selectable restrictor portion adapted to be selectively positioned by the user in a plurality of user selectable positions, the user selectable restrictor portion including only a single valve to control a flow of the pressurized gas provided to the nasal portion and the mouth portion so as to limit a flow of the pressurized gas out of the mouth portion to be up to but no more than the flow of the pressurized gas provided out of the nasal portion to the nares of the user for each of the plurality of user selectable positions, wherein the user selectable restrictor portion includes at least one of (i) a first flow position in which the flow of the pressurized gas out of the mouth portion is the same as the flow of the pressurized gas out of the nasal portion, and (ii) a plurality of second flow positions in which the flow of the pressurized gas out of the mouth portion is less than the flow of the pressurized gas out of the nasal portion.

29. The retrofit kit of claim 28, wherein the nasal portion includes a frame portion having at least one supplemental gas port.

30. The retrofit kit of claim 29, wherein the air delivery tube is connected to the at least one supplemental gas port to deliver the pressurized gas from the nasal portion to the mouth portion.

31. The retrofit kit of claim 28, wherein the structure adapted to connect the nasal portion to the mouth portion includes a support having a threaded portion and a dial adapted to engage the threaded portion, the dial and the threaded portion being adapted to adjust a position of the mouth portion relative to the nasal portion by turning of the dial.

32. A patient interface for delivery of a supply of air at positive pressure from a source of pressurised breathable air, the patient interface comprising:

a breathing arrangement including a first chamber and a second chamber in direct communication with the first chamber, the breathing arrangement structured to allow a first flow rate of air to a nasal cavity of a patient from the first chamber via a first orifice and a second flow rate of air to an oral cavity of the patient from the second chamber via a second orifice; and a flow limitation structure adapted to be selectively positioned by the patient in a plurality of user selectable positions, the flow limitation structure including a user selectable restrictor portion having only a single valve structured and arranged to control a flow of the pressurized air to the first chamber and the second chamber so as to allow a flow of air to the second chamber at a rate that exceeds a rate required for pressure equalisation between the first and second chamber and restrict the second flow rate of air to the patient via the second orifice to an amount that is up to but no greater than the first flow rate of air to the patient via the first orifice for each of the plurality of user selectable positions.

33. The patient interface of claim 32, wherein the single valve is positioned in a fluid communication passageway between the first chamber and the second chamber.

34. The patient interface of claim 32, wherein the flow limitation structure includes at least one of a (i) a first flow position in which the second flow rate of air to the patient via the second orifice is the same as the first flow rate of air to the patient via the first orifice, and (ii) a plurality of second flow positions in which the second flow rate of air to the patient via the second orifice is less than the first flow rate of air to the patient via the first orifice.

* * * * *